United States Patent
Van Der Veen et al.

(10) Patent No.: US 8,653,097 B2
(45) Date of Patent: Feb. 18, 2014

(54) TETRA-AZA-HETEROCYCLES AS PHOSPHATIDYLINOSITOL-3-KINASES (P13-KINASES) INHIBITOR

(75) Inventors: Lars Van Der Veen, Vienna (AT); Darryl McConnell, Vienna (AT); Tobias Wunberg, Hinterbruehl (AT)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 259 days.

(21) Appl. No.: 13/124,513

(22) PCT Filed: Oct. 15, 2009

(86) PCT No.: PCT/EP2009/063491
§ 371 (c)(1),
(2), (4) Date: Jun. 1, 2011

(87) PCT Pub. No.: WO2010/043676
PCT Pub. Date: Apr. 22, 2010

(65) Prior Publication Data
US 2011/0312940 A1    Dec. 22, 2011

(30) Foreign Application Priority Data
Oct. 17, 2008    (EP) .................................... 08166873

(51) Int. Cl.
*A61K 31/437* (2006.01)
*A61K 31/519* (2006.01)
*C07D 471/16* (2006.01)
*C07D 487/16* (2006.01)

(52) U.S. Cl.
USPC ............. 514/293; 544/242; 544/251; 546/79; 546/82; 514/279; 514/267

(58) Field of Classification Search
USPC .......... 546/26, 79, 81, 82; 514/279, 292, 293, 514/247, 267; 544/242, 245, 251
See application file for complete search history.

(56) References Cited

U.S. PATENT DOCUMENTS

| | | | |
|---|---|---|---|
| 7,517,995 B2 | 4/2009 | Breitfelder et al. | |
| 7,691,888 B2 | 4/2010 | Betzemeier et al. | |
| 8,163,763 B2 * | 4/2012 | Bergeron et al. | .......... 514/264.1 |
| 2006/0100245 A1 | 5/2006 | Betzemeier et al. | |
| 2006/0106013 A1 | 5/2006 | Breitfelder et al. | |
| 2007/0238730 A1 | 10/2007 | Breitfelder et al. | |
| 2009/0156554 A1 | 6/2009 | Breitfelder et al. | |
| 2010/0113414 A1 | 5/2010 | Betzemeier et al. | |

FOREIGN PATENT DOCUMENTS

| | | |
|---|---|---|
| EP | 1 241 170 A2 | 9/2002 |
| WO | 2005/005438 A1 | 1/2005 |
| WO | 2006/040279 A1 | 4/2006 |
| WO | 2006/040281 A1 | 4/2006 |
| WO | 2007/115931 A1 | 10/2007 |

OTHER PUBLICATIONS

Ameriks, Michael K., et al; Small Molecule Inhibitors of Phosphoinositide 3-Kinase (P13K) δ and γ; Current Topics in Medicinal Chemistry (2009) vol. 9 pp. 738-753.
Chen, Yulong L., et al; Inhibition of P13K/Akt Signaling: An Emerging Paradigm for Targeted Cancer Therapy; Curr. Med. Chem—Cancer Agents (2005) vol. 5 pp. 575-589.
International Search Report for PCT/EP2009/063491 mailed Dec. 17, 2011.
Larsen, Scott D.; Novel Parham-Type Cycloacylations of 1H-Pyrazole-1-Alkanoic Acids; Synlett (1997) pp. 1013-1014.
Wermuth, Camille G; Molecular Variations Based on Isosteric Replacements; Practice of Medicinal Chemistry (1996) pp. 203-237.

\* cited by examiner

*Primary Examiner* — Golam M M Shameem
(74) *Attorney, Agent, or Firm* — Michael P. Morris; Edward S. Lazer

(57) ABSTRACT

The present invention encompasses compounds of general formula (1) wherein $R^1$ to $R^4$, A, X, m and k are defined as in claim 1, which are suitable for the treatment of diseases characterized by excessive or abnormal cell proliferation, and the use thereof for preparing a medicament having the above-mentioned properties.

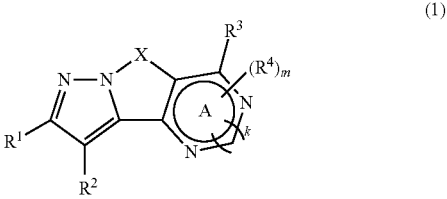

(1)

9 Claims, No Drawings

TETRA-AZA-HETEROCYCLES AS PHOSPHATIDYLINOSITOL-3-KINASES (PI3-KINASES) INHIBITOR

The present invention relates to new tetra-aza-heterocycles of general formula (1)

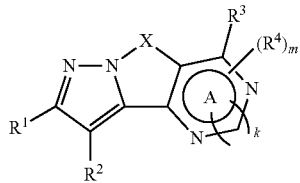

wherein the groups $R^1$ to $R^4$, A, X, m and k have the meanings given in the claims and specification, the isomers thereof, processes for preparing these tetra-aza-heterocycles and their use as medicaments.

BACKGROUND TO THE INVENTION

A number of protein kinases have already proved to be suitable target molecules for therapeutic intervention in a variety of indications, e.g. cancer and inflammatory and autoimmune diseases. Since a high percentage of the genes involved in the development of cancer which have been identified thus far encode kinases, these enzymes are attractive target molecules for the therapy of cancer in particular.

Phosphatidylinositol-3-kinases (PI3-kinases) are a subfamily of the lipid kinases which catalyse the transfer of a phosphate group to the 3'-position of the inositol ring of phosphoinositides.

They play an important role in numerous cell processes such as e.g. cell growth and differentiation processes, the control of cytoskeletal changes and the regulation of intracellular transport processes. On the basis of their in vitro specificity for certain phosphoinositide substrates the PI3-kinases can be divided into different categories.

DETAILED DESCRIPTION OF THE INVENTION

It has now surprisingly been found that compounds of general formula (1), wherein the groups $R^1$ to $R^4$, A, X, m and k have the meanings given below, act as inhibitors of specific kinases. Thus, the compounds according to the invention may be used for example for the treatment of diseases connected with the activity of kinases and characterised by excessive or abnormal cell proliferation.

The present invention relates to compounds of general formula (1)

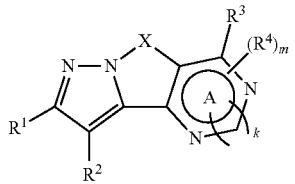

wherein
$R^1$, $R^2$, $R^3$ and $R^4$ independently of one another denote $R^5$; and
A denotes an aromatic ring; and
X is an optionally substituted C1-C3 alkylidene chain wherein one or two non-adjacent methylene units are independently optionally replaced by C(O), C(O)NR$^g$R$^g$, NR$^g$C(O), SO, SO$_2$, NR$^g$SO$_2$, SO$_2$NR$^g$R$^g$, O, S, or NR$^g$R$^g$; and
m and k independently denote 0 or 1; and
each $R^5$ denotes a group selected from among $R^a$, $R^b$ and $R^a$ substituted by one or more identical or different $R^b$ and/or $R^c$; and
each $R^a$ independently of one another denotes hydrogen or a group optionally substituted by one or more identical or different $R^b$ and/or $R^c$, selected from among $C_{1-6}$alkyl, 2-6 membered heteroalkyl, $C_{1-6}$haloalkyl, $C_{3-10}$cycloalkyl, $C_{4-16}$cycloalkylalkyl, $C_{6-10}$aryl, $C_{7-16}$arylalkyl, 5-12 membered heteroaryl, 6-18 membered heteroarylalkyl, 3-14 membered heterocycloalkyl and 4-14 membered heterocycloalkylalkyl,
each $R^b$ denotes a suitable group and is selected independently of one another from among =O, —OR$^c$, $C_{1-3}$haloalkyloxy, —OCF$_3$, =S, —SR$^c$, =NR$^c$, =NOR$^c$, =NNR$^c$R$^c$, =NN(R$^g$)C(O)NR$^c$R$^c$, —NR$^c$R$^c$, —ONR$^c$R$^c$, —N(OR$^c$)R$^c$, —N(R$^g$)NR$^c$R$^c$, halogen, —CF$_3$, —CN, —NC, —OCN, —SCN, —NO, —NO$_2$, =N$_2$, —N$_3$, —S(O)R$^c$, —S(O)OR$^c$, —S(O)$_2$R$^c$, —S(O)$_2$OR$^c$, —S(O)NR$^c$R$^c$, —S(O)$_2$NR$^c$R$^c$, —OS(O)R$^c$, —OS(O)OR$^c$, —OS(O)$_2$R$^c$, —OS(O)$_2$OR$^c$, —OS(O)NR$^c$R$^c$, —OS(O)$_2$NR$^c$R$^c$, —C(O)R$^c$, —C(O)OR$^c$, —C(O)SR$^c$, —C(O)NR$^c$R$^c$, —C(O)N(R$^g$)NR$^c$R$^c$, —C(O)N(R$^g$)OR$^c$, —C(NR$^g$)NR$^c$R$^c$, —C(NOH)R$^c$, —C(NOH)NR$^c$R$^c$, —OC(O)R$^c$, —OC(O)OR$^c$, —OC(O)SR$^c$, —OC(O)NR$^c$R$^c$, —OC(NR$^g$)NR$^c$R$^c$, —SC(O)R$^c$, —SC(O)OR$^c$, —SC(O)NR$^c$R$^c$, —SC(NR$^g$)NR$^c$R$^c$, —N(R$^g$)C(O)R$^c$, —N[C(O)R$^c$]$_2$, —N(OR$^g$)C(O)R$^c$, —N(R$^g$)C(NR$^g$)R$^c$, —N(R$^g$)N(R$^g$)C(O)R$^c$, —N[C(O)R$^c$]NR$^c$R$^c$, —N(R$^g$)C(S)R$^c$, —N(R$^g$)S(O)R$^c$, —N(R$^g$)S(O)OR$^c$, —N(R$^g$)S(O)$_2$R$^c$, —N[S(O)$_2$R$^c$]$_2$, —N(R$^g$)S(O)$_2$OR$^c$, —N(R$^g$)S(O)$_2$NR$^c$R$^c$, —N(R$^g$)[S(O)$_2$]$_2$R$^c$, —N(R$^g$)C(O)OR$^c$, —N(R$^g$)C(O)SR$^c$, —N(R$^g$)C(O)NR$^c$R$^c$, —N(R$^g$)C(O)NR$^g$NR$^c$R$^c$, —N(R$^g$)N(R$^g$)C(O)NR$^c$ R$^c$, —N(R$^g$)C(S)NR$^c$R$^c$, —[N(R$^g$)C(O)]$_2$R$^c$, —N(R$^g$)[C(O)]$_2$R$^c$, —N{[C(O)]$_2$R$^c$}$_2$, —N(R$^g$)[C(O)]$_2$OR$^c$, —N(R$^g$)[C(O)]$_2$NR$^c$R$^c$, —N{[C(O)]$_2$OR$^c$}$_2$, —N{[C(O)]$_2$NR$^c$R$^c$}$_2$, —[N(R$^g$)C(O)]$_2$OR$^c$, —N(R$^g$)C(NR$^g$)OR$^c$, —N(R$^g$)C(NOH)R$^c$, —N(R$^g$)C(NR$^g$)SR$^c$, —N(R$^g$)C(NR$^g$)NR$^c$R$^c$ and —N═C(R$^g$)NR$^c$R$^c$ and each $R^c$ independently of one another denotes hydrogen or a group optionally substituted by one or more identical or different $R^d$ and/or $R^e$, selected from among $C_{1-6}$alkyl, 2-6 membered heteroalkyl, $C_{1-6}$haloalkyl, $C_{3-10}$cycloalkyl, $C_{4-16}$cycloalkylalkyl, $C_{6-10}$aryl, $C_{7-16}$arylalkyl, 5-12 membered hetero-aryl, 6-18 membered heteroarylalkyl, 3-14 membered heterocycloalkyl and 4-14 membered heterocycloalkylalkyl, and
each $R^d$ denotes a suitable group and is selected independently of one another from among =O, —OR$^e$, $C_{1-3}$haloalkyloxy, —OCF$_3$, =S, —SR$^e$, =NR$^e$, =NOR$^e$, =NNR$^e$R$^e$, =NN(R$^g$)C(O)NR$^e$R$^e$, —NR$^e$R$^e$, —ONR$^e$R$^e$, —N(R$^g$)NR$^e$R$^e$, halogen, —CF$_3$, —CN, —NC, —OCN, —SCN, —NO, —NO$_2$, =N$_2$, —N$_3$, —S(O)R$^e$, —S(O)OR$^e$, —S(O)$_2$R$^e$, —S(O)$_2$OR$^e$, —S(O)NR$^e$R$^e$, —S(O)$_2$NR$^e$R$^e$, —OS(O)R$^e$, —OS(O)$_2$R$^e$, —OS(O)$_2$OR$^e$, —OS(O)NR$^e$R$^e$, —OS(O)$_2$NR$^e$R$^e$, —C(O)R$^e$, —C(O)OR$^e$, —C(O)SR$^e$, —C(O)NR$^e$R$^e$, —C(O)N(R$^g$)NR$^e$R$^e$, —C(O)N(R$^g$)OR$^e$, —C(NR$^g$)NR$^e$R$^e$, —C(NOH)R$^c$, —C(NOH)NR$^e$R$^e$, —OC(O)R$^e$, —OC(O)OR$^e$, —OC(O)SR$^e$, —OC(O)NR$^e$R$^e$, —OC(NR$^g$)NR$^e$R$^e$, —SC(O)R$^e$, —SC(O)OR$^e$, —SC(O)NR$^e$R$^e$, —SC(NR$^g$)NR$^e$ R$^e$, —N(R$^g$)C(O)R$^e$, —N[C(O)R$^e$]$_2$, —N(OR$^g$)C(O)R$^e$, —N(R$^g$)C(NR$^g$)R$^e$, —N(R$^g$)N(R$^g$)C(O)R$^e$, —N[C(O)R$^e$] NR$^e$R$^e$, —N(R$^g$)C(S)R$^e$, —N(R$^g$)S(O)R$^e$, —N(R$^g$)S(O) OR$^e$, —N(R$^g$)S(O)$_2$R$^e$, —N[S(O)$_2$R$^e$]$_2$, —N(R$^g$)S(O)$_2$OR$^e$, —N(R$^g$)S(O)$_2$NR$^e$R$^e$, —N(R$^g$)[S(O)$_2$]$_2$R$^e$, —N(R$^g$)C(O)

$OR^e$, —$N(R^g)C(O)SR^e$, —$N(R^g)C(O)NR^eR^e$, —$N(R^g)C(O)NR^gNR^eR^e$, —$N(R^g)N(R^g)C(O)NR^eR^e$, —$N(R^g)C(S)NR^eR^e$, —$[N(R^g)C(O)]_2R^e$, —$N(R^g)[C(O)]_2R^e$, —$N\{[C(O)]_2R^e\}_2$, —$N(R^g)[C(O)]_2OR^e$, —$N(R^g)[C(O)]_2NR^eR^e$, —$N\{[C(O)]_2OR^e\}_2$, —$N\{[C(O)]_2NR^eR^e\}_2$, —$[N(R^g)C(O)]_2OR^e$, —$N(R^g)C(NR^g)OR^e$, —$N(R^g)C(NOH)R^e$, —$N(R^g)C(NR^g)SR^e$, —$N(R^g)C(NR^g)NR^eR^e$ and —$N$=$C(R^g)NR^eR^e$ each $R^e$ independently of one another denotes hydrogen or a group optionally substituted by one or more identical or different $R^f$ and/or $R^g$, selected from among $C_{1-6}$alkyl, 2-6 membered heteroalkyl, $C_{1-6}$haloalkyl, $C_{3-10}$cycloalkyl, $C_{4-16}$cycloalkylalkyl, $C_{6-10}$aryl, $C_{7-16}$arylalkyl, 5-12 membered hetero-aryl, 6-18 membered heteroarylalkyl, 3-14 membered heterocycloalkyl and 4-14 membered heterocycloalkylalkyl, and each $R^f$ denotes a suitable group and in each case is selected independently of one another from among =O, —$OR^g$, $C_{1-3}$haloalkyloxy, —$OCF_3$, —$SR^g$, =$NR^g$, —$NOR^g$, =$NNR^gR^g$, =$NN(R^h)C(O)NR^gR^g$, —$NR^gR^g$, —$ONR^gR^g$, —$N(R^h)NR^gR^g$, halogen, —$CF_3$, —$CN$, —$NC$, —$OCN$, —$SCN$, —$NO$, —$NO_2$, =$N_2$, —$N_3$, —$S(O)R^g$, —$S(O)OR^g$, —$S(O)_2R^g$, —$S(O)_2OR^g$, —$S(O)NR^gR^g$, —$S(O)_2NR^gR^g$, —$OS(O)R^g$, —$OS(O)_2R^g$, —$OS(O)_2OR^g$, —$OS(O)NR^gR^g$, —$OS(O)_2NR^gR^g$, —$C(O)R^g$, —$C(O)OR^g$, —$C(O)SR^g$, —$C(O)NR^gR^g$, —$C(O)N(R^h)NR^gR^g$, —$C(O)N(R^h)OR^g$, —$C(NR^h)NR^gR^g$, —$C(NOH)R^g$, —$C(NOH)NR^gR^g$, —$OC(O)R^g$, —$OC(O)OR^g$, —$OC(O)SR^g$, —$OC(O)NR^gR^g$, —$OC(NR^h)NR^gR^g$, —$SC(O)R^g$, —$SC(O)OR^g$, —$SC(O)NR^gR^g$, —$SC(NR^h)NR^gR^g$, —$N(R^h)C(O)R^g$, —$N[C(O)R^g]_2$, —$N(OR^h)C(O)R^g$, —$N(R^h)C(NR^h)R^g$, —$N(R^h)N(R^h)C(O)R^g$, —$N[C(O)R^g]NR^gR^g$, —$N(R^h)C(S)R^g$, —$N(R^h)S(O)R^g$, —$N(R^h)S(O)OR^g$, —$N(R^h)S(O)_2R^g$, —$N[S(O)_2R^g]_2$, —$N(R^h)S(O)_2OR^g$, —$N(R^h)S(O)_2NR^gR^g$, —$N(R^h)[S(O)_2]_2R^g$, —$N(R^h)C(O)OR^g$, —$N(R^h)C(O)SR^g$, —$N(R^h)C(O)NR^gR^g$, —$N(R^h)C(O)NR^hNR^gR^g$, —$N(R^h)N(R^h)C(O)NR^gR^g$, —$N(R^h)C(S)NR^gR^g$, —$[N(R^h)C(O)]_2R^g$, —$N(R^h)[C(O)]_2R^g$, —$N\{[C(O)]_2R^g\}_2$, —$N(R^h)[C(O)]_2OR^g$, —$N(R^h)[C(O)]_2NR^gR^g$, —$N\{[C(O)]_2OR^g\}_2$, —$N\{[C(O)]_2NR^gR^g\}_2$, —$[N(R^h)C(O)]_2OR^g$, —$N(R^h)C(NR^h)OR^g$, —$N(R^h)C(NOH)R^g$, —$N(R^h)C(NR^h)SR^g$, —$N(R^h)C(NR^h)NR^gR^g$; and —$N$=$C(R^h)NR^hR^h$; and each $R^g$ independently of one another denotes hydrogen or a group optionally substituted by one or more identical or different $R^h$, selected from among $C_{1-6}$alkyl, 2-6 membered heteroalkyl, $C_{1-6}$haloalkyl, $C_{3-10}$cycloalkyl, $C_{4-16}$cycloalkylalkyl, $C_{6-10}$aryl, $C_{7-16}$arylalkyl, 5-12 membered hetero-aryl, 6-18 membered heteroarylalkyl, 3-14 membered heterocycloalkyl and 4-14 membered heterocycloalkylalkyl; and each $R^h$ is selected independently of one another from among hydrogen, $C_{1-6}$alkyl, 2-6 membered heteroalkyl, $C_{1-6}$haloalkyl, $C_{3-10}$cycloalkyl, $C_{4-16}$cycloalkylalkyl, $C_{6-10}$aryl, $C_{7-16}$arylalkyl, 5-12 membered heteroaryl, 6-18 membered heteroarylalkyl, 3-14 membered heterocycloalkyl and 4-14 membered heterocycloalkylalkyl, optionally in the form of the prodrugs, the tautomers, the racemates, the enantiomers, the diastereomers, the prodrugs and the mixtures thereof, and optionally the pharmacologically acceptable salts thereof.

One aspect of the invention relates to compounds of general formulae (1), wherein X is selected from the group consisting of —$CH_2$—, —$(CH_2)_2$— and —$(CH_2)_3$—, optionally substituted by $C_{1-6}$alkyl.

Another aspect of the invention relates to compounds of general formula (1), wherein $R^3$ is a radical selected from the group consisting of $C_{6-10}$aryl and 5-12 membered Heteroaryl, optionally substituted by one or more $R^4$.

Another aspect of the invention relates to compounds of general formula (1), wherein $R^3$ is pyridyl, pyrimidyl or pyrazolyl.

Another aspect of the invention relates to compounds of general formula (1), wherein $R^3$ is substituted by a residue selected from the group consisting of halogen, —$CN$, —$OR^c$, —$NR^cR^c$ and $C_{1-6}$alkyl optionally substituted by $R^b$.

Another aspect of the invention relates to compounds of general formula (1), wherein $R^3$ is hydrogen.

Another aspect of the invention relates to compounds of general formula (1), wherein $R^1$ is selected from the group consisting of —$NHC(O)R^c$, —$NHC(O)OR^c$, —$NHC(O)NR^cR^c$ and —$C(O)NR^cR^c$.

Another aspect of the invention relates to compounds of general formula (1), wherein $R^1$ is —$NHC(O)CH_3$.

Another aspect of the invention relates to compounds of general formula (1), wherein $R^4$ is selected from the group consisting of $C_{1-6}$alkyl, $C_{3-10}$cycloalkyl, $C_{6-10}$aryl, 5-12 membered heteroaryl and 3-14 membered heterocycloalkyl.

One aspect of the invention relates to compounds of general formula (1), or the pharmacologically effective salts thereof, as medicaments.

One aspect of the invention relates to compounds of general formula (1), or the pharmacologically effective salts thereof, for preparing a medicament with an antiproliferative activity.

One aspect of the invention is a pharmaceutical preparations, containing as active substance one or more compounds of general formula (1), or the pharmacologically effective salts thereof, optionally in combination with conventional excipients and/or carriers.

One aspect of the invention is the use of compounds of general formula (1) for preparing a medicament for the treatment and/or prevention of cancer, infections, inflammatory and autoimmune diseases.

One aspect of the invention is a pharmaceutical preparation comprising a compound of general formula (1) and at least one other cytostatic or cytotoxic active substance, different from formula (1), optionally in the form of the tautomers, the racemates, the enantiomers, the diastereomers and the mixtures thereof, as well as optionally the pharmacologically acceptable salts thereof.

The following Examples illustrate the present invention without restricting its scope.

DEFINITIONS

As used herein the following definitions apply, unless stated otherwise.

By alkyl substituents are meant in each case saturated, unsaturated, straight-chain or branched aliphatic hydrocarbon groups (alkyl group) and this includes both saturated alkyl groups and unsaturated alkenyl and alkynyl groups. Alkenyl substituents are in each case straight-chain or branched, unsaturated alkyl groups, which have at least one double bond. By alkynyl substituents are meant in each case straight-chain or branched, unsaturated alkyl groups, which have at least one triple bond.

The term heteroalkyl refers to groups which can be derived from alkyl as defined above in its broadest sense by replacing one or more of the groups —$CH_3$ in the hydrocarbon chains independently of one another by the groups —OH, —SH or —$NH_2$, one or more of the groups —$CH_2$— independently of one another by the groups —O—, —S— or —NH—, one or more of the groups by the group 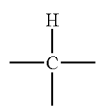

one or more of the groups =CH— by the group =N—, one or more of the groups =CH$_2$ by the group =NH or one or more of the groups =CH by the group =N, while in all only a maximum of three heteroatoms may be present in a heteroalkyl, there must be at least one carbon atom between two oxygen and between two sulphur atoms or between one oxygen and one sulphur atom and the group as a whole must have chemical stability.

It flows from the indirect definition/derivation from alkyl that heteroalkyl is made up of the sub-groups of saturated hydrocarbon chains with hetero-atom(s), heteroalkenyl and heteroalkynyl, while further subdivision into straight-chain (unbranched) and branched may be carried out. If a heteroalkyl is supposed to be substituted, the substitution may take place independently of one another, in each case mono- or polysubstituted, at all the hydrogen-carrying oxygen, sulphur, nitrogen and/or carbon atoms. Heteroalkyl itself may be linked to the molecule as substituent both through a carbon atom and through a heteroatom.

By way of example, the following representative compounds are listed: dimethylaminomethyl; dimethylaminoethyl (1-dimethylaminoethyl; 2-dimethylaminoethyl); dimethylaminopropyl (1-dimethylaminopropyl, 2-dimethylaminopropyl, 3-dimethylaminopropyl); diethylaminomethyl; diethylaminoethyl (1-diethylaminoethyl, 2-diethylaminoethyl); diethylaminopropyl (1-diethylaminopropyl, 2-diethylamino-propyl, 3-diethylaminopropyl); diisopropylaminoethyl (1-diisopropylaminoethyl, 2-di-isopropylaminoethyl); bis-2-methoxyethylamino; [2-(dimethylamino-ethyl)-ethyl-amino]-methyl; 3-[2-(dimethylamino-ethyl)-ethyl-amino]-propyl; hydroxymethyl; 2-hydroxyethyl; 3-hydroxypropyl; methoxy; ethoxy; propoxy; methoxymethyl; 2-methoxyethyl etc.

The term alkylidene chain refers to a straight or branched carbon chain that may be fully saturated or have one or more units of unsaturation and has two points of attachment to the rest of the molecule, wherein one or more methylene units may optionally and independently be replaced with a group including, but not limited to —C(O)—, —C(O)NR$^g$—, —NR$^g$C(O)—, —S(O)—, —S(O)$_2$—, —NR$^g$SO$_2$—, —SO$_2$NR$^g$—, —O—, —S—, or —NR$^g$—.

Haloalkyl relates to alkyl groups, wherein one or more hydrogen atoms are replaced by halogen atoms. Haloalkyl includes both saturated alkyl groups and unsaturated alkenyl and alkynyl groups, such as for example —CF$_3$, —CHF$_2$, —CH$_2$F, —CF$_2$CF$_3$, —CHFCF$_3$, —CH$_2$CF$_3$, —CF$_2$CH$_3$, —CHFCH$_3$, —CF$_2$CF$_2$CF$_3$, —CF$_2$CH$_2$CH$_3$, —CF=CF$_2$, —CCl=CH$_2$, —CBr=CH$_2$, —CI=CH$_2$, —C≡C—CF$_3$, —CHFCH$_2$CH$_3$ and —CHFCH$_2$CF$_3$.

Halogen refers to fluorine, chlorine, bromine and/or iodine atoms.

By cycloalkyl is meant a mono or bicyclic ring, while the ring system may be a saturated ring or, however, an unsaturated, non-aromatic ring, which may optionally also contain double bonds, such as for example cyclopropyl, cyclopropenyl, cyclobutyl, cyclobutenyl, cyclopentyl, cyclopentenyl, cyclo hexyl, cyclohexenyl, norbornyl and norbornenyl.

Cycloalkylalkyl includes a non-cyclic alkyl group wherein a hydrogen atom bound to a carbon atom, usually to a terminal C atom, is replaced by a cycloalkyl group.

Aryl relates to monocyclic or bicyclic aromatic rings with 6-10 carbon atoms such as phenyl and naphthyl, for example.

Arylalkyl includes a non-cyclic alkyl group wherein a hydrogen atom bound to a carbon atom, usually to a terminal C atom, is replaced by an aryl group.

By heteroaryl are meant mono- or bicyclic aromatic rings, which instead of one or more carbon atoms contain one or more, identical or different hetero atoms, such as e.g. nitrogen, sulphur or oxygen atoms. Examples include furyl, thienyl, pyrrolyl, oxazolyl, thiazolyl, isoxazolyl, isothiazolyl, pyrazolyl, imidazolyl, triazolyl, tetrazolyl, oxadiazolyl, thiadiazolyl, pyridyl, pyrimidyl, pyridazinyl, pyrazinyl and triazinyl. Examples of bicyclic heteroaryl groups are indolyl, isoindolyl, benzofuryl, benzothienyl, benzoxazolyl, benzothiazolyl, benzisoxazolyl, benzisothiazolyl, benzimidazolyl, indazolyl, isoquinolinyl, quinolinyl, quinoxalinyl, cinnolinyl, phthalazinyl, quinazolinyl and benzotriazinyl, indolizinyl, oxazolopyridyl, imidazopyridyl, naphthyridinyl, indolinyl, isochromanyl, chromanyl, tetrahydroisoquinolinyl, isoindolinyl, isobenzotetrahydrofuryl, isobenzotetrahydrothienyl, isobenzothienyl, benzoxazolyl, pyridopyridyl, benzotetrahydrofuryl, benzotetrahydrothienyl, purinyl, benzodioxolyl, triazinyl, phenoxazinyl, phenothiazinyl, pteridinyl, benzothiazolyl, imidazopyridyl, imidazothiazolyl, dihydrobenzisoxazinyl, benzisoxazinyl, benzoxazinyl, dihydrobenzisothiazinyl, benzopyranyl, benzothiopyranyl, coumarinyl, isocoumarinyl, chromonyl, chromanonyl, pyridyl-N-oxide tetrahydroquinolinyl, dihydroquinolinyl, dihydroquinolinonyl, dihydroisoquinolinonyl, dihydrocoumarinyl, dihydroisocoumarinyl, isoindolinonyl, benzodioxanyl, benzoxazolinonyl, pyrrolyl-N-oxide, pyrimidinyl-N-oxide, pyridazinyl-N-oxide, pyrazinyl-N-oxide, quinolinyl-N-oxide, indolyl-N-oxide, indolinyl-N-oxide, isoquinolyl-N-oxide, quinazolinyl-N-oxide, quinoxalinyl-N-oxide, phthalazinyl-N-oxide, imidazolyl-N-oxide, isoxazolyl-N-oxide, oxazolyl-N-oxide, thiazolyl-N-oxide, indolizinyl-N-oxide, indazolyl-N-oxide, benzothiazolyl-N-oxide, benzimidazolyl-N-oxide, pyrrolyl-N-oxide, oxadiazolyl-N-oxide, thiadiazolyl-N-oxide, triazolyl-N-oxide, tetrazolyl-N-oxide, benzothiopyranyl-S-oxide and benzothiopyranyl-S,S-dioxide.

Heteroarylalkyl encompasses a non-cyclic alkyl group wherein a hydrogen atom bound to a carbon atom, usually to a terminal C atom, is replaced by a heteroaryl group.

Heterocycloalkyl relates to saturated or unsaturated, non-aromatic mono-, bicyclic or bridged bicyclic rings comprising 3-12 carbon atoms, which instead of one or more carbon atoms carry heteroatoms, such as nitrogen, oxygen or sulphur. Examples of such heterocyloalkyl groups are tetrahydrofuryl, pyrrolidinyl, pyrrolinyl, imidazolidinyl, imidazolinyl, pyrazolidinyl, pyrazolinyl, piperidinyl, piperazinyl, indolinyl, isoindolinyl, morpholinyl, thiomorpholinyl, homomorpholinyl, homopiperidinyl, homopiperazinyl, homothiomorpholinyl, thiomorpholinyl-S-oxide, thiomorpholinyl-S,S-dioxide, tetrahydropyranyl, tetrahydrothienyl, homothiomorpholinyl-S,S-dioxide, oxazolidinonyl, dihydropyrazolyl, dihydropyrrolyl, dihydropyrazinyl, dihydropyridyl, dihydropyrimidinyl, dihydrofuryl, dihydropyranyl, tetrahydrothienyl-S-oxide, tetrahydrothienyl-S,S-dioxide, homothiomorpholinyl-S-oxide, 2-oxa-5-azabicyclo[2,2,1]heptane, 8-oxa-3-azabicyclo[3.2.1]octane, 3,8-diaza-bicyclo[3.2.1]octane, 2,5-diaza-bicyclo[2,2,1]heptane, 3.8-diaza-bicyclo[3.2.1]octane, 3.9-diaza-bicyclo[4.2.1]nonane and 2.6-diaza-bicyclo[3.2.2]nonane.

Heterocycloalkylalkyl relates to a non-cyclic alkyl group wherein a hydrogen atom bound to a carbon atom, usually to a terminal C atom, is replaced by a heterocycloalkyl group.

Intermediates:

The substituted or unsubstituted 5,6-dihydro-pyrrolo[1,2-b]pyrazol-4-ones, 6,7-dihydro-5H-pyrazolo[1,5-a]pyridin-4-ones, and 5,6,7,8-tetrahydro-pyrazolo[1,5-a]azepin-4-ones used herein as starting materials can be synthesized according to literature procedures such as described in but not limited to Larsen, Scott D. Synlett 1997, 1013 and EP1241170.

General Procedure A1: Formation of keto-ene-amines from N,N-dimethylformamide dimethyl acetal The monoketone is taken up in DMA, N,N-dimethylformamide dimethyl acetal (5-10 eq.) is added and the reaction mixture is heated at 150° C. for 5 min using microwaves or heated classically at 130° C. for 1-3 h. After cooling the reaction mixture to RT, the precipitated product is filtered off and dried in vacuo at 40° C. The product can be used without further purification.

General Procedure A2: Formation of 1,3-diketones from Acid Chlorides

Under inert atmosphere the monoketone is added to dry THF and the reaction mixture is cooled to −78° C. LHMDS (3 eq.) is slowly added to the reaction mixture so that the reaction temperature is kept below −60° C. After completion of the addition, a solution of the acid chloride (1-2 eq.) in dry THF is added slowly. The reaction mixture is stirred overnight allowing it to warm to RT. For the work-up the mixture is cooled to −20° C. and the reaction is quenched with diluted hydrochloric acid and phosphate buffer (consisting of 22 g $NaH_2PO_4$ and 87 g $Na_2HPO_4$ in 530 mL $H_2O$) resulting in a final pH of about 6. Ethyl acetate is added and the organic layer is separated. The aqueous phase is extracted with ethyl acetate, the combined organic phases are dried over $MgSO_4$, filtered and the solvent is removed under reduced pressure. The remaining solids are triturated with MTBE or EtOH. The product may be purified by flash column chromatography (silicagel) or used without further purification.

General Procedure A3: Formation of 1,3-diketones from Active Esters a) Formation of the Active Ester Carboxylic acid is dissolved in DCM or DCE, CDI (1 eq.) is added and the reaction mixture is stirred at RT over night. The solvent is removed under reduced pressure and the crude product is used without further purification.

b) Formation of the Diketone

A 1 M solution of LHMDS (3 eq.) in THF is diluted with THF and the resulting solution is cooled to −10° C. under inert atmosphere. The monoketone is added in small portions so that the reaction temperature is kept below −10° C. After stirring one additional hour at −10° C., a solution of the active ester (1-2 eq.) in THF is added slowly. The reaction mixture is stirred overnight allowing it to warm to RT. The reaction is quenched with an aqueous saturated ammonium chloride solution and the aqueous phase is extracted twice with DCM. The combined organic layers are dried over $MgSO_4$, filtered and the solvent is removed under reduced pressure. The remaining solids are triturated with MTBE or EtOH. The product may be purified by flash column chromatography (silicagel) or used without further purification.

A-1) N-{5-[1-Dimethylamino-meth-(Z/E)-ylidene]-4-oxo-4,5,6,7-tetrahydro-pyrazolo[1,5-a]pyridin-2-yl}-acetamide

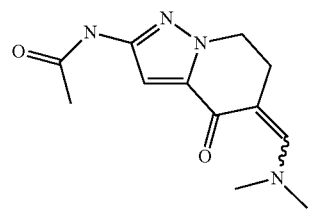 [SMILES: CC(=O)Nc1cc2n(n1)CCC(=CN(C)C)C2=O]

A-01a) (4-Oxo-4,5,6,7-tetrahydro-pyrazolo[1,5-a]pyridin-2-yl)-carbamic acid tert-butyl ester

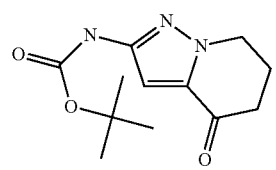 [SMILES: CC(C)(C)OC(=O)Nc1cc2n(n1)CCCC2=O]

To a solution of 4-oxo-4,5,6,7-tetrahydro-pyrazolo[1,5-a]pyridine-2-carboxylic acid (2.56 g, 14.2 mmol, prepared according to EP1241170) in 160 mL dry toluene is added triethylamine (2.38 mL, 17.1 mmol) and diphenylphosphoryl azide (3.68 mL, 17.1 mmol) and the reaction mixture is stirred overnight at RT. Then tert-butanol (26.7 mL, 74.1 mmol) is added and the reaction is heated to 120° C. for 5 h. The solvents are removed under reduced pressure and the residue is purified by flash column chromatography (silica gel, 0-70% ethyl acetate in cyclohexane). Yield: 2.32 g. HPLC-MS: $R_t$=1.55 min, $(M+H-56)^+$=196. $^1$H NMR (DMSO-d6): δ 9.8 (s, 1H), 6.7 (s, 1H), 4.2 (t, 2H), 2.6 (t, 2H), 2.3 (quint, 2H), 1.4 (s, 9H).

A-01b) 2-Amino-6,7-dihydro-5H-pyrazolo[1,5-a]pyridin-4-one

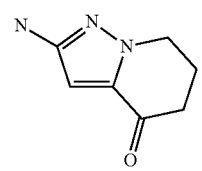 [SMILES: Nc1cc2n(n1)CCCC2=O]

To a solution of A-01a (4.50 g, 17.9 mmol) in 20 mL dioxane 22 mL of a 4M solution of HCl in dioxane are added and the reaction mixture is stirred at 60° C. for 2 h. The reaction mixture is cooled to RT and filtered. The solids are washed with dioxane and dried in vacuo. Yield: 2.77 g. HPLC-MS: $R_t$=0.49 min, $(M+H)^+$=152. $^1$H NMR (DMSO-d6): δ 6.5 (s, 1H), 4.3 (t, 2H), 2.7 (t, 2H), 2.3 (quint, 2H).

A-01c) N-(4-Oxo-4,5,6,7-tetrahydro-pyrazolo[1,5-a]pyridin-2-yl)-acetamide

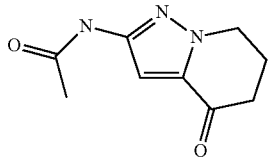

Under cooling with a water bath acetyl chloride (0.98 mL, 14 mmol) is added slowly to a mixture of A-01b (1.74 g, 11.5 mmol) and DBU (3.4 mL, 23 mmol) in 10 mL ACN and the reaction mixture is stirred for 2 h at RT. An aqueous saturated solution of NaHCO$_3$ is added and the reaction mixture is extracted with ethyl acetate. The combined organic phases are washed with brine, dried on MgSO$_4$ and the solvents are removed under reduced pressure. The residue is purified by flash column chromatography (silica gel, 0-10% MeOH in DCM). Yield: 1.60 g. HPLC-MS: R$_t$=0.19 min, (M+H)$^+$=194. $^1$H NMR (DMSO-d6): δ 10.6 (s, 1H), 6.9 (s, 1H), 4.2 (t, 2H), 2.6 (t, 2H), 2.3 (quint, 2H), 2.2 (s, 3H).

A-01 is prepared using general procedure A1 starting from A-01c (0.60 g, 3.1 mmol).

Yield: 0.43 g. HPLC-MS: R$_t$=1.6 min, (M+H)$^+$=249.

A-02) N-{5-[1-Dimethylamino-meth-(Z/E)-ylidene]-4-oxo-5,6,7,8-tetrahydro-4H-pyrazolo[1,5-a]azepin-2-yl}-acetamide

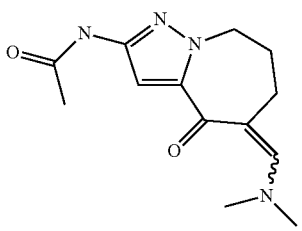 [SMILES: CC(=O)Nc1cc2n(n1)CCCC(=CN(C)C)C2=O]

A-02a) (4-Oxo-5,6,7,8-tetrahydro-4H-pyrazolo[1,5-c]azepin-2-yl)-carbamic acid tert-butyl ester

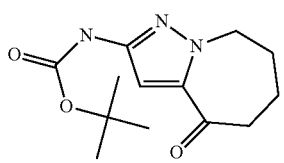 [SMILES: CC(C)(C)OC(=O)Nc1cc2n(n1)CCCCC2=O]

At 120° C. diphenylphosphoryl azide (3.85 mL, 17.8 mmol) is added dropwise to a solution of 4-oxo-5,6,7,8-tetrahydro-4H-pyrazolo[1,5-a]azepine-2-carboxylic acid (3.15 g, 16.2 mmol, prepared according to EP1241170) and sodium tert-butoxide (1.56 g, 16.2 mmol) in 60 mL tert-butanol and the reaction mixture is stirred for 2 h. The reaction mixture is cooled to RT and filtered. The solids are washed with toluene and the filtrate is concentrated under reduced pressure. The residue is purified by flash column chromatography (silica gel, 0-70% ethyl acetate in cyclohexane). Yield: 2.16 g. HPLC-MS: R$_t$=1.69 min, (M−H)$^-$=264. $^1$H NMR (DMSO-d6): δ 9.7 (s, 1H), 6.7 (s, 1H), 4.4 (t, 2H), 2.8 (t, 2H), 2.0 (quint, 2H), 1.8 (quint, 2H), 1.4 (s, 9H).

A-02b) 2-Amino-5,6,7,8-tetrahydro-pyrazolo[1,5-a]azepin-4-one

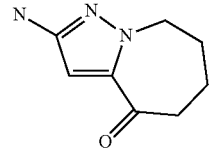

A0-2b is prepared analogously to A-01b starting from A-02a (0.94 g, 3.54 mmol).

Yield: 0.42 g. HPLC-MS: R$_t$=0.89 min, (M+H)$^+$=166.

A-02c) N-(4-Oxo-5,6,7,8-tetrahydro-4H-pyrazolo[1,5-a]azepin-2-yl)-acetamide

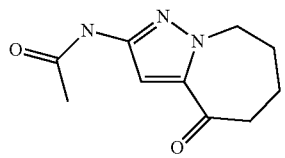

To a solution of A-02b (1.6 g, 9.7 mmol) in 15 mL acetic acid is added acetic anhydride (1.8 mL, 19 mmol) and the reaction mixture is stirred at 95° C. for 2 h. Water is added and the reaction mixture is neutralized with an aqueous saturated solution of NaHCO$_3$ and extracted with ethyl acetate containing 10% MeOH. The combined organic phases are dried on MgSO$_4$ and the solvents are removed under reduced pressure. The residue is lyophilized. Yield: 1.84 g. HPLC-MS: R$_t$=1.69 min, (M+H)$^+$=208. $^1$H NMR (DMSO-d6): δ 10.5 (s, 1H), 6.9 (s, 1H), 4.4 (t, 2H), 2.8 (t, 2H), 2.0 (m, 5H), 1.9 (quint, 2H).

A-02 is prepared using general procedure A1 starting from A-02c (1.84 g, 3.1 mmol).

Yield: 0.77 g. HPLC-MS: R$_t$=1.64 min, (M+H)$^+$=263.

A-03) 5-[1-Dimethylamino-meth-(Z/E)-ylidene]-4-oxo-4,5,6,7-tetrahydro-pyrazolo[1,5-a]pyridine-2-carboxylic acid ethyl ester

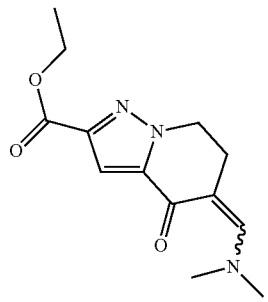 [SMILES: CCOC(=O)c1cc2n(n1)CCC(=CN(C)C)C2=O]

A-03a) 4-Oxo-4,5,6,7-tetrahydro-pyrazolo[1,5-a]pyridine-2-carboxylic acid ethyl ester

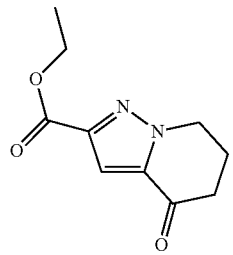

To a mixture of 4-oxo-4,5,6,7-tetrahydro-pyrazolo[1,5-a]pyridine-2-carboxylic acid (16 g, 89 mmol) in 170 mL EtOH is added slowly 12 mL concentrated sulphuric acid and the reaction mixture is heated to 100° C. for 2 h. The reaction mixture is cooled to RT and concentrated under reduced pressure. The residue is poured on ice, neutralized by the addition of an aqueous saturated solution of NaHCO$_3$ and extracted with DCM. The combined organic phases are washed with water and brine, dried on MgSO$_4$ and the solvent are removed under reduced pressure. Yield: 17 g. HPLC-MS: R$_t$=1.79 min, (M+H)$^+$=209.

A-03 is prepared using general procedure A1 starting from A-03a (5.00 g, 24.0 mmol). After cooling down the reaction mixture is concentrated under reduced pressure and then worked up with water and ethyl acetate. Yield: 6.22 g. HPLC-MS: R$_t$=1.82 min, (M+H)$^+$=264.

A-04) [5-(2-Acetylamino-4-oxo-4,5,6,7-tetrahydro-pyrazolo[1,5-a]pyridine-5-carbonyl)-pyridin-2-yl]-ethyl-carbamic acid tert-butyl ester

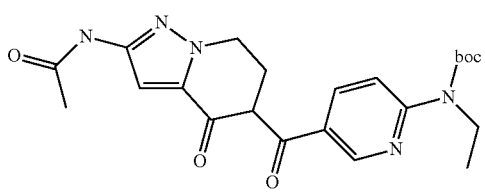

A-04a)
6-(tert-Butoxycarbonyl-ethyl-amino)-nicotinic acid

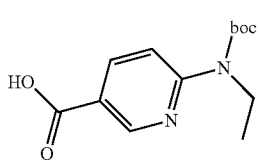

6-Chloro-nicotinic acid methyl ester (60 g, 0.35 mol) is taken up in 500 mL 2M ethylamine in THF and stirred at 100° C. in a sealed tube for 16 h. The reaction mixture is cooled to RT and the solvents are removed under reduced pressure. The residue is poured on ice and stirred for 15 min. The precipitate is filtered off, washed with water and dried in vacuo. The dried 6-ethylamino-nicotinic acid methyl ester (30 g, 0.17 mol) is dissolved in 150 mL DCM and triethylamine (29 mL, 0.20 mol), DMAP (4.0 g, 33 mmol) and di-tert-butyl to dicarbonate (91.7 g, 0.42 mol) are added successively at 0° C. The reaction mixture is allowed to warm up to RT and stirred for 16 h. To the reaction mixture 100 mL of 10% citric acid in water is added and the reaction mixture is stirred for 10 min. The organic phase is separated, dried over Na$_2$SO$_4$ and concentrated under reduced pressure. Yield: 60 g. The crude 6-(tert-butoxycarbonyl-ethyl-amino)-nicotinic acid methyl ester is taken up in 100 mL dioxane and a solution of lithium hydroxide monohydrate (13.5 g, 0.32 mol) in 100 mL is added and the reaction mixture is stirred at RT for 4 h. The dioxane is removed from the reaction mixture under reduced pressure, water is added and the reaction mixture is acidified to pH 6 with a solution of 10% citric acid in water. The formed precipitate is filtered off and dried in vacuo. Yield: 36 g. $^1$H NMR (DMSO-d6): δ 13.2 (s, 1H), 8.8 (s, 1H), 8.2 (d, 1H), 7.8 (d, 1H), 4.0 (quart, 2H), 1.5 (s, 9H), 1.2 (t, 3H).

A-04b) (5-Chlorocarbonyl-pyridin-2-yl)-ethyl-carbamic acid tert-butyl ester

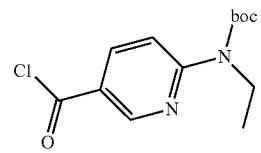

A-04a (0.80 g, 3.0 mmol) is taken up in 18 mL DCE, 1-chloro-N,N-2-trimethylpropenylamine (0.80 mL, 6.0 mmol) is added and the reaction mixture is stirred overnight at RT. The reaction mixture is concentrated under reduced pressure and the crude product is used in the next step without purification.

A-04 is prepared using general procedure A2 starting from A-1c (0.35 g, 1.8 mmol) and A-04b (3.0 mmol). Yield: 1.0 g, content 60%. HPLC-MS: R$_t$=2.19/2.29 min, (M+H)$^+$=442.

A-05) N-[5-(6-Chloro-pyridine-3-carbonyl)-4-oxo-4,5,6,7-tetrahydro-pyrazolo[1,5-a]pyridin-2-yl]-acetamide

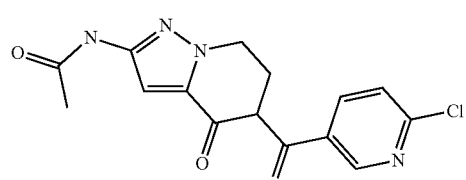

A-05 is prepared using general procedure A2 starting from A-01c (8.44 g, 43.7 mmol) and 6-chloro-nicotinoyl chloride (13.1 g, 74.3 mmol). Yield: 4.85 g, content 40%. HPLC-MS: R$_t$=1.96/1.99 min, (M+H)$^+$=333/335.

A-06) 5-[6-(tert-Butoxycarbonyl-ethyl-amino)-pyridine-3-carbonyl]-4-oxo-4,5,6,7-tetrahydro-pyrazolo[1,5-a]pyridine-2-carboxylic acid

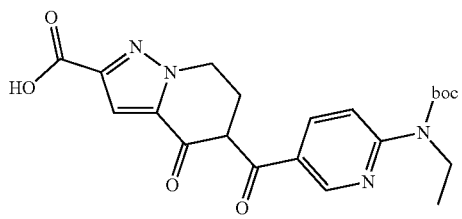

A-06 is prepared using general procedure A2 starting from 4-oxo-4,5,6,7-tetrahydro-pyrazolo[1,5-a]pyridine-2-carboxylic acid (0.50 g, 2.8 mmol) and A-04b (1.34 g, 4.72 mmol). Yield: 0.76 g. HPLC-MS: $R_t$=2.23/2.31 min, $(M+H)^+$=429.

A-07) 5-(6-Chloro-pyridine-3-carbonyl)-4-oxo-4,5,6,7-tetrahydro-pyrazolo[1,5-a]pyridine-2-carboxylic acid

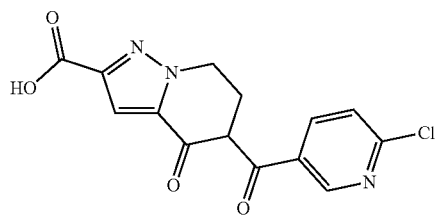 [SMILES: O=C(O)c1cc2n(n1)CCC(C(=O)c1ccc(Cl)nc1)C2=O]

A-07 is prepared using general procedure A2 starting from 4-oxo-4,5,6,7-tetrahydro-pyrazolo[1,5-a]pyridine-2-carboxylic acid (5.00 g, 27.8 mmol) and 6-chloro-nicotinoyl chloride (7.33 g, 41.6 mmol). Yield: 7.37 g. HPLC-MS: Rt=1.94 min, $(M+H)^+$=320/322.

A-08) N-[5-(6-Methyl-pyridine-3-carbonyl)-4-oxo-4,5,6,7-tetrahydro-pyrazolo[1,5-a]pyridin-2-yl]-acetamide

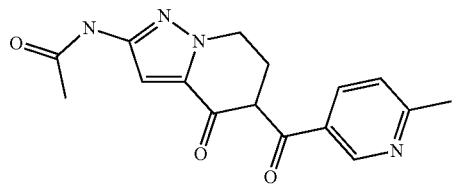 [SMILES: CC(=O)Nc1cc2n(n1)CCC(C(=O)c1ccc(C)nc1)C2=O]

To a mixture of sodium tert-pentoxide (4.22 g, 38.4 mmol) in 12 mL DMSO is added A-01c (2.47 g, 12.8 mmol) and the reaction mixture is stirred for 0.5 h at RT. 6-Methyl-nicotinic acid methyl ester (2.71 g, 17.9 mmol) is dissolved in 2.5 mL DMSO and added drop-wise to the reaction mixture over a period of 1 h. The reaction mixture is stirred for 0.5 h and than poured out in 50 mL water containing acetic acid (3.1 mL, 54 mmol). The reaction mixture is extracted with ethyl acetate and the combined organic phases are dried over MgSO₄ and concentrated under reduced pressure. Yield: 5.59 g, content 60%. HPLC-MS: $R_t$=1.73 min, $(M+H)^+$=313.

A-09) N-tert-Butoxycarbonyl-[5-(2-Acetylamino-4-oxo-4,5,6,7-tetrahydro-pyrazolo[1,5-a]pyridine-5-carbonyl)-pyridin-2-yl]-carbamic acid tert-butyl ester

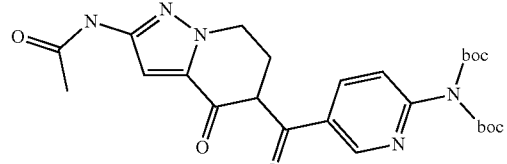

A-09a)
6-[N,N-Di-(tert-butoxycarbonyl)-amino]-nicotinic acid

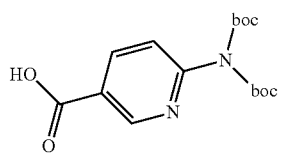

6-Amino-nicotinic acid methyl ester (13.7 g, 90.0 mmol), triethylamine (12.5 mL, 90.0 mmol) and DMAP (3.30 g, 27.0 mmol) are taken up in 200 mL DCM and a solution of di-tert-butyl dicarbonate (41.3 g, 189 mmol) in 40 mL DCM is added drop wise. The reaction mixture is stirred overnight at RT. An aqueous 5% KHSO₄ solution is added and the reaction mixture is extracted with DCM. The combined organic phases are washed with an aqueous 50% saturated KHCO₃ solution, dried over MgSO₄ and concentrated under reduced pressure. Yield: 34.9 g.

Of this residue 17.3 g is taken up in a mixture of 150 mL MeOH and 300 mL water, lithium hydroxide (2.33 g, 97.3 mmol) is added and the reaction mixture is stirred for 3 h at RT. The reaction mixture is acidified to pH 4 with acetic acid and the formed precipitate is filtered off, washed with water and dried in vacuo. Yield: 11.8 g. ¹H NMR (DMSO-d6): δ 9.0 (s, 1H), 8.2 (d, 1H), 7.2 (d, 2H), 1.4 (s, 18H).

A-09b) N-tert-Butoxycarbonyl-(5-chlorocarbonyl-pyridin-2-yl)-carbamic acid tert-butyl ester

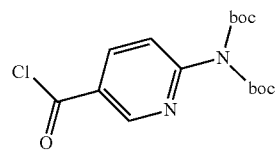

A-09a (5.00 g, 14.8 mmol) is dried by azeotropic distillation with toluene and then taken up in 20 mL dry THF and cooled to 0° C. 1-Chloro-N,N-2-trimethylpropenyl-amine (3.95 g, 30.0 mmol) is added drop wise and the reaction mixture is stirred at RT for 3 h. The reaction mixture is concentrated under reduced pressure and the crude product is used in the next step without purification.

A-09 is prepared using general procedure A2 starting from A-01c (2.50 g, 12.9 mmol) and A-09b (6.93 g, 19.4 mmol). Yield: 2.65 g. HPLC-MS: $R_t$=2.51/2.57 min, $(M+H)^+$=514.

A-10) N-[5-(6-Chloro-pyridine-3-carbonyl)-4-oxo-5,6,7,8-tetrahydro-4H-pyrazolo[1,5-a]azepin-2-yl]-acetamide

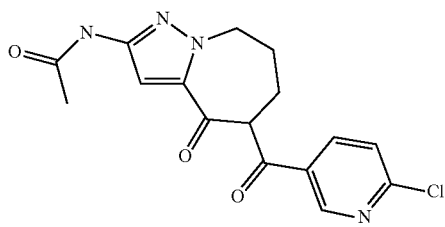 [SMILES: CC(=O)Nc1cc2n(n1)CCCC(C(=O)c1ccc(Cl)nc1)C2=O]

A-10 is prepared using general procedure A2 starting from A-02c (1.15 g, 5.55 mmol) and 6-chloro-nicotinoyl chloride (1.47 g, 8.32 mmol). Yield: 0.36 g. HPLC-MS: $R_t$=2.01 min, $(M+H)^+$=347/349.

A-11) 2-Methyl-5-(1-trityl-1H-imidazole-4-carbonyl)-5,6,7,8-tetrahydro-pyrazolo[1,5-a]azepin-4-one

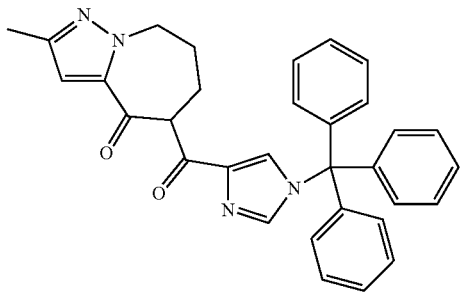 [SMILES: Cc1cc2n(n1)CCCC(C(=O)c1cn(C(c3ccccc3)(c3ccccc3)c3ccccc3)cn1)C2=O]

A-11a) 2-Methyl-4-oxo-5,6,7,8-tetrahydro-4H-pyrazolo[1,5-c]azepine-5-carboxylic acid ethyl ester

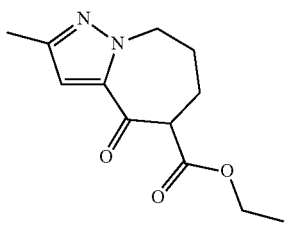 [SMILES: CCOC(=O)C1CCCn2nc(C)cc2C1=O]

A mixture of 5-methyl-2H-pyrazole-3-carboxylic acid ethyl ester (15 g, 97.3 mmol), potassium carbonate (20.2 g, 146 mmol) and ethyl 5-bromovalerate (17.1 mL, 107 mmol) in 150 mL acetonitrile is heated to reflux and stirred for 2 h. The reaction mixture is cooled to RT, concentrated under reduced pressure, taken up in 200 mL dichloromethane and washed three times with 100 mL water. The organic phase is dried over MgSO₄ and concentrated under reduced pressure. Yield: 24.4 g, mixture of regeo-isomers. The isomeric product is taken up in 280 mL toluene, potassium tert-butoxide (14.8 g, 107 mmol) is added and the reaction mixture is heated to reflux and stirred for 3.5 h. The reaction mixture is cooled to RT and extracted with 100 mL water. The water phase is acidified to pH6 with 6N HCl and the precipitated solids are filtered off and dried in vacuo. Yield: 4.87 g. HPLC-MS: $R_t$=2.20 min, $(M+H)^+$=237.

A-11b) 2-Methyl-5,6,7,8-tetrahydro-pyrazolo[1,5-c]azepin-4-one

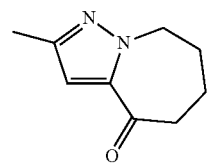

A-11a (4.69 g, 19.9 mmol) is taken up in 36 mL 4N HCl, heated to reflux and stirred for 2 h. The reaction mixture is cooled to RT and concentrated under reduced pressure. Yield: 4.64 g. HPLC-MS: $R_t$=1.81 min, $(M+H)^+$=165.

A-11c) 1-Trityl-1H-imidazole-4-carbonyl chloride

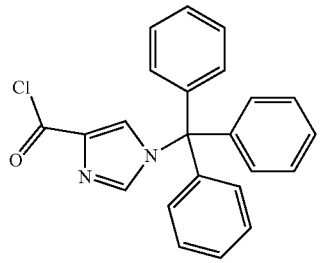 [SMILES: O=C(Cl)c1cn(C(c2ccccc2)(c2ccccc2)c2ccccc2)cn1]

Methyl-4-imidazolecarboxylate (9.20 g, 73.0 mmol) is taken up in 130 mL dichloromethane and triethylamine (20.2 mL, 146 mmol) and chlorotriphenylmethane (22.4 g, 80.2 mmol) are added. The reaction mixture is stirred overnight at RT. The reaction mixture is washed with an aqueous 5% NaHCO₃ solution and the organic phase is dried over MgSO₄ and concentrated under reduced pressure. Yield: 26.9 g, mixture of regeo-isomers. The isomeric product is taken up in 80 mL methanol, a solution of lithium hydroxide (3.50 g, 24.0 mmol) in 100 mL water is added drop-wise and the reaction mixture is stirred overnight at RT. The reaction mixture is acidified to pH4 with acetic acid and extracted once with 200 mL and once with 100 mL dichloromethane. The organic phases are combined, dried over MgSO$_4$ and concentrated under reduced pressure. The residue is triturated with 100 mL cyclohexane containing 10% ethyl acetate. Yield: 10.5 g, mixture of regeoisomers. The isomeric product (3.00 g, 8.47 mmol) is taken up in 5 mL dry THF and 1-chloro-N,N-2-trimethylpropenylamine (2.15 mL, 16.1 mL) and 1 mL dimethylacetamide are added. The reaction mixture is stirred for 0.5 h at RT and concentrated under reduced pressure. Yield: 3.2 g.

A-11 is prepared using general procedure A2 starting from A-11b (0.50 g, 3.0 mmol) and A-11c (2.84 g, 7.61 mmol). Yield: 5.0 g, content max. 30%. HPLC-MS: R$_t$=2.61 min, (M−H)$^-$=499.

A-12) 5-Dimethylaminomethylene-2-phenyl-6,7-dihydro-5H-pyrazolo[1,5-a]pyridin-4-one

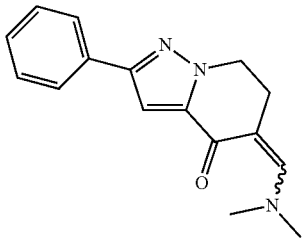 [SMILES: CN(C)C=C1CCn2nc(-c3ccccc3)cc2C1=O]

A-12a) 2-(3-Ethoxycarbonyl-propyl)-5-phenyl-2H-pyrazole-3-carboxylic acid methyl ester

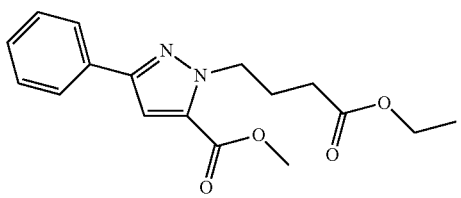 [SMILES: CCOC(=O)CCCn1nc(-c2ccccc2)cc1C(=O)OC]

5-Phenyl-2H-pyrazole-3-carboxylic acid methyl ester (9.10 g, 45.0 mmol) is taken up in 100 mL acetonitrile and heated to 60° C. Ethyl 4-bromobutanoate (8.78 g, 45.0 mmol) and potassium carbonate (8.09 g, 58.5 mmol) are added and the reaction mixture is heated to 85° C. and stirred under reflux for 5 h. The reaction mixture is filtered and the filtrate is concentrated under reduced pressure. The residue is taken up in water and extracted with ethyl acetate. The combined organic phases are dried over Na$_2$SO$_4$ and concentrated under reduced pressure. The residue is purified by flash column chromatography (silica gel, 8-40% ethyl acetate in heptane). Yield: 10.3 g. Rf (silica gel, 2% methanol in DCM)=0.41.

A-12b) 2-Phenyl-6,7-dihydro-5H-pyrazolo[1,5-c]pyridin-4-one

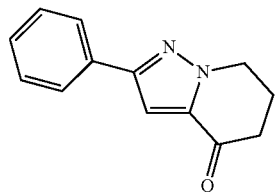 [SMILES: O=C1CCCn2nc(-c3ccccc3)cc21]

At 80° C. A-12a (10.0 g, 31.6 mmol) in 200 mL toluene is added over a period of 3 h to a mixture of potassium tert-butoxide (4.26 g, 37.9 mmol) in 150 mL toluene. After complete addition the reaction mixture is stirred for another h at 90° C. and then poured into 3 M HCl. The reaction mixture is extracted with ethyl acetate and the combined organic phases are concentrated under reduced pressure. The residue is taken up in 50 mL dioxane, 150 mL 6 N HCl is added and the reaction mixture is stirred at 90° C. for 3 h. The reaction mixture is neutralized with sodium bicarbonate and extracted with ethyl acetate. The combined organic phases are dried over Na$_2$SO$_4$ and concentrated under reduced pressure. The residue is purified by flash column chromatography (silica gel, 20-43% ethyl acetate in heptane). Yield: 2.5 g. HPLC-MS: R$_t$=1.96 min, (M+H)$^+$=213.

A-12 is prepared using general procedure A1 starting from A-12b (0.60 g, 2.83 mmol). Yield: 1.2 g (crude). HPLC-MS: R$_t$=1.86 min, (M+H)$^+$=268.

EXAMPLES

Examples B-01 to B-16 are synthesized according to general procedure B1 or B2. The appropriate keto-ene-amine or diketone and hydrazine required for synthesis can be deduced from the table of examples.

General Procedure B1:

The appropriate keto-ene-amine or 1,3-diketone (1 eq.) and the appropriate hydrazine or hydrazine salt (1-5 eq.) are taken up in acetic acid and the reaction is heated to 90° C. for 1 to 5 h. The acetic acid is removed under reduced pressure and the residue is taken up in water. The reaction mixture is neutralized to pH 5-6 with aqueous 2M NaOH and extracted with DCM. The combined organic phases are washed with water and brine, dried on MgSO$_4$ and the solvents are removed under reduced pressure. The product may be purified by NP or RP column chromatography.

General Procedure B2:

The appropriate 1,3-diketone (1 eq.) and the appropriate hydrazine or hydrazine salt (1-5 eq.) are taken up in pyridine and the reaction is heated to 60° C. for 1 to 16 h. The pyridine is removed under reduced pressure and the residue is taken up in water. The reaction mixture is acidified to pH 5-6 with 5% citric acid in water and extracted with DCM. The combined organic phases are washed with water and brine, dried on MgSO$_4$ and the solvents are removed under reduced pressure. The product may be purified by NP or RP column chromatography and protecting groups may have to be removed.

TABLE 1

Example B-01-B-32

| No. | Structure | Keto-ene-amine or 1,3-diketone | Hydrazine salt | M + H | R$_t$ (min) |
|---|---|---|---|---|---|
| B-01 | 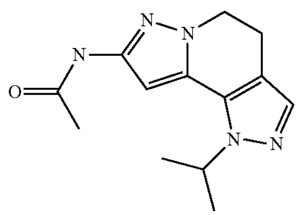 [SMILES: CC(=O)Nc1cc2n(n1)CCc1cnn(C(C)C)c1-2] | A-01 | isopropyl-hydrazine hydrochloride | 260 | 1.10 |
| B-02 | 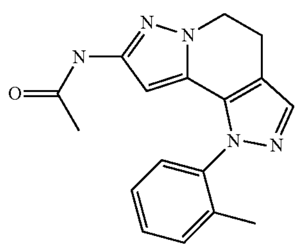 [SMILES: CC(=O)Nc1cc2n(n1)CCc1cnn(-c3ccccc3C)c1-2] | A-01 | ortho-tolyl-hydrazine hydrochloride | 308 | 1.29 |
| B-03 | 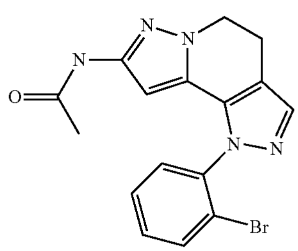 | A-01 | 2-bromophenyl-hydrazine hydrochloride | 372/374 | 1.30 |
| B-04 | 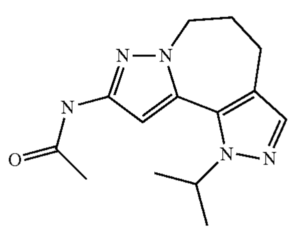 [SMILES: CC(=O)Nc1cc2n(n1)CCCc1cnn(C(C)C)c1-2] | A-02 | isopropyl-hydrazine hydrochloride | 274 | 1.08 |
| B-05 | 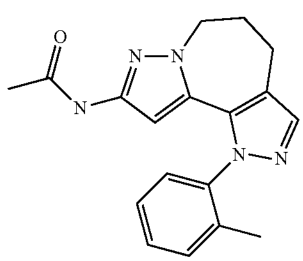 [SMILES: CC(=O)Nc1cc2n(n1)CCCc1cnn(-c3ccccc3C)c1-2] | A-02 | ortho-tolyl-hydrazine hydrochloride | 322 | 1.31 |
| B-06 | 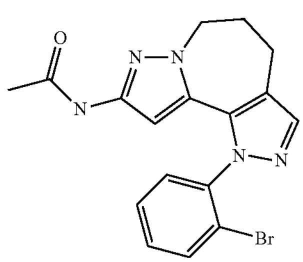 [SMILES: CC(=O)Nc1cc2n(n1)CCCc1cnn(-c3ccccc3Br)c1-2] | A-02 | 2-bromophenyl-hydrazine hydrochloride | 386/388 | 1.30 |

TABLE 1-continued

Example B-01-B-32

| No. | Structure | Keto-ene-amine or 1,3-diketone | Hydrazine salt | M + H | R$_t$ (min) |
|---|---|---|---|---|---|
| B-07 | 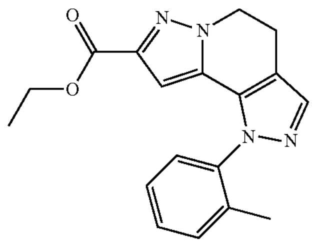 [SMILES: CCOC(=O)c1cc2n(n1)CCc1cnn(-c3ccccc3C)c1-2] | A-03 | ortho-tolyl-hydrazine hydrochloride | 323 | 1.61 |
| B-08 | 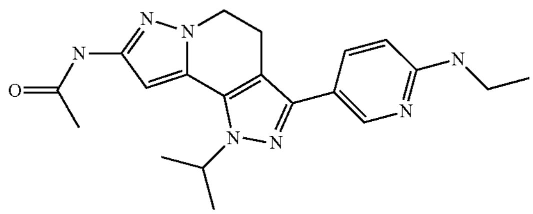 | A-04 | isopropyl-hydrazine hydrochloride | 380 | 1.45 |
| B-09 | 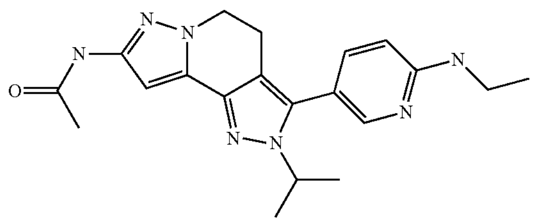 [SMILES: CCNc1ccc(-c2c3c(nn2C(C)C)-c2cc(NC(C)=O)nn2CC3)cn1] | A-04 | isopropyl-hydrazine hydrochloride | 380 | 1.39 |
| B-10 | 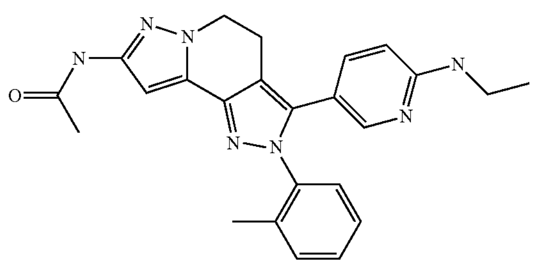 [SMILES: CCNc1ccc(-c2c3c(nn2-c2ccccc2C)-c2cc(NC(C)=O)nn2CC3)cn1] | A-04 | ortho-tolyl-hydrazine hydrochloride | 428 | 1.51 |
| B-11 | 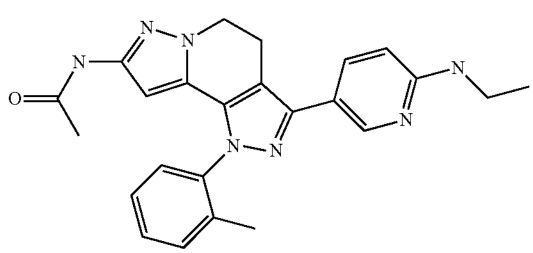 [SMILES: CCNc1ccc(-c2nn(-c3ccccc3C)c3c2CCn2nc(NC(C)=O)cc2-3)cn1] | A-04 | ortho-tolyl-hydrazine hydrochloride | 428 | 1.64 |
| B-12 | 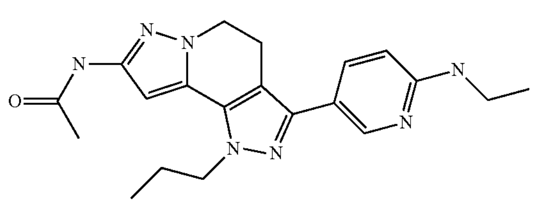 [SMILES: CCCn1nc(-c2ccc(NCC)nc2)c2c1-c1cc(NC(C)=O)nn1CC2] | A-04 | n-propyl-hydrazine oxalate | 380 | 1.49 |

TABLE 1-continued

Example B-01-B-32

| No. | Structure | Keto-ene-amine or 1,3-diketone | Hydrazine salt | M + H | R$_t$ (min) |
|---|---|---|---|---|---|
| B-13 | 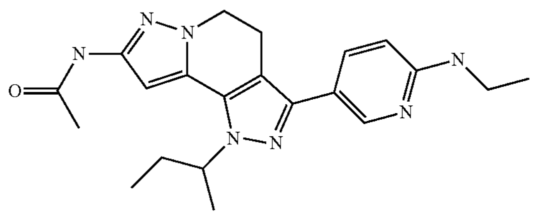 [SMILES: CCNc1ccc(-c2nn(C(C)CC)c3c2CCn2nc(NC(C)=O)cc2-3)cn1] | A-04 | sec-butyl-hydrazine | 394 | 1.63 |
| B-14 | 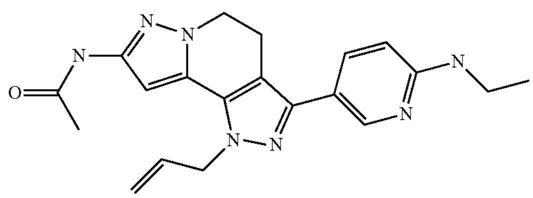 [SMILES: C=CCn1nc(-c2ccc(NCC)nc2)c2c1-c1cc(NC(C)=O)nn1CC2] | A-04 | prop-1-enyl-hydrazine sulfate | 378 | 1.45 |
| B-15 | 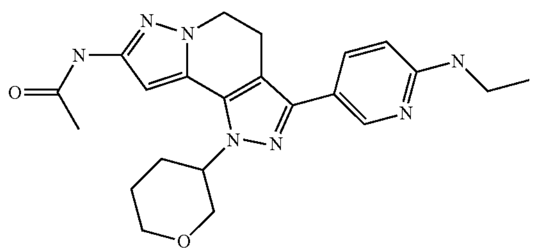 [SMILES: CCNc1ccc(-c2nn(C3CCCOC3)c3c2CCn2nc(NC(C)=O)cc2-3)cn1] | A-04 | (tetrahydro-pyran-3-yl)-hydrazine hydrochloride | 422 | 1.47 |
| B-16 | 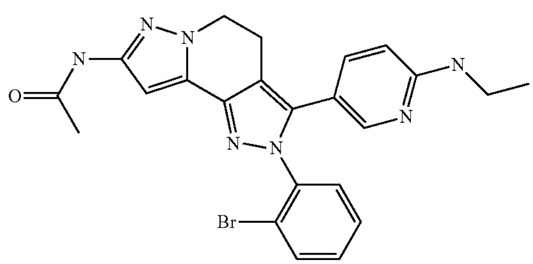 [SMILES: CCNc1ccc(-c2c3c(nn2-c2ccccc2Br)-c2cc(NC(C)=O)nn2CC3)cn1] | A-04 | (2-bromo-phenyl)-hydrazine hydrochloride | 492/494 | 1.58 |
| B-17 | 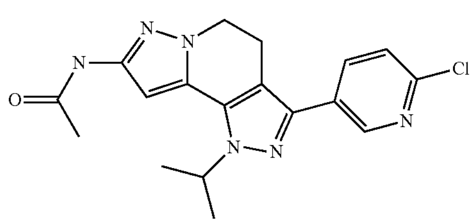 [SMILES: CC(=O)Nc1cc2n(n1)CCc1c(-c3ccc(Cl)nc3)nn(C(C)C)c1-2] | A-05 | isopropyl-hydrazine hydrochloride | 371/373 | 1.69 |
| B-18 | 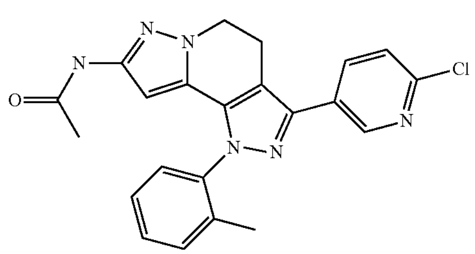 [SMILES: CC(=O)Nc1cc2n(n1)CCc1c(-c3ccc(Cl)nc3)nn(-c3ccccc3C)c1-2] | A-05 | ortho-tolyl-hydrazine hydrochloride | 419/421 | 1.77 |

TABLE 1-continued

Example B-01-B-32

| No. | Structure | Keto-ene-amine or 1,3-diketone | Hydrazine salt | M + H | R$_t$ (min) |
|---|---|---|---|---|---|
| B-19 | 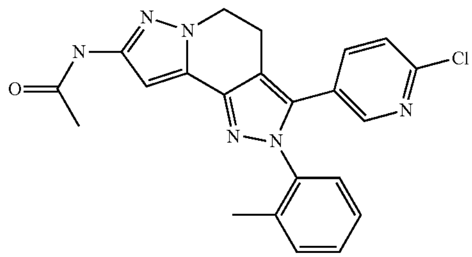 [SMILES: CC(=O)Nc1cc2n(n1)CCc1c-2nn(-c2ccccc2C)c1-c1ccc(Cl)nc1] | A-05 | ortho-tolyl-hydrazine hydrochloride | 419/421 | 1.71 |
| B-20 | 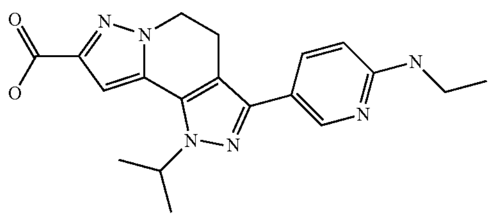 [SMILES: CCNc1ccc(-c2nn(C(C)C)c3c2CCn2nc(C(=O)O)cc2-3)cn1] | A-06 | isopropyl-hydrazine hydrochloride | 367 | 1.05 |
| B-21 | 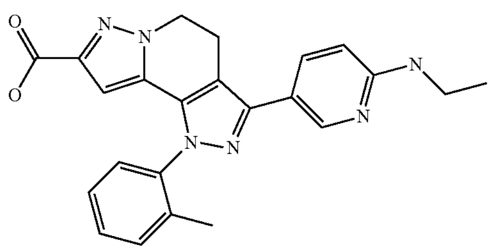 [SMILES: CCNc1ccc(-c2nn(-c3ccccc3C)c3c2CCn2nc(C(=O)O)cc2-3)cn1] | A-06 | ortho-tolyl-hydrazine hydrochloride | 415 | 1.14 |
| B-22 | 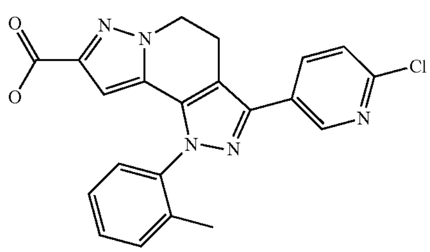 [SMILES: Cc1ccccc1-n1nc(-c2ccc(Cl)nc2)c2c1-c1cc(C(=O)O)nn1CC2] | A-07 | ortho-tolyl-hydrazine hydrochloride | 406/408 | 2.16 |
| B-23 | 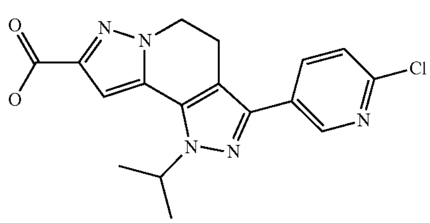 [SMILES: CC(C)n1nc(-c2ccc(Cl)nc2)c2c1-c1cc(C(=O)O)nn1CC2] | A-07 | isopropyl-hydrazine hydrochloride | 358/360 | 2.15 |
| B-24 | 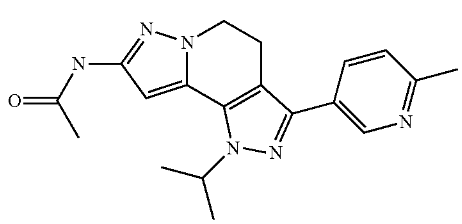 [SMILES: CC(=O)Nc1cc2n(n1)CCc1c(-c3ccc(C)nc3)nn(C(C)C)c1-2] | A-08 | isopropyl-hydrazine hydrochloride | 351 | 1.47 |

TABLE 1-continued

Example B-01-B-32

| No. | Structure | Keto-ene-amine or 1,3-diketone | Hydrazine salt | M + H | R_t (min) |
|---|---|---|---|---|---|
| B-25 | 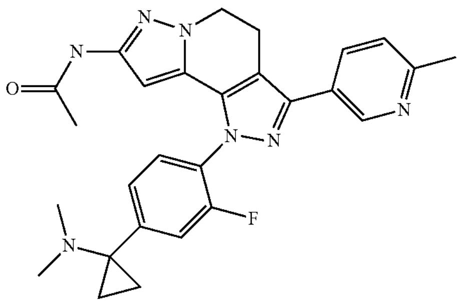 [SMILES: CC(=O)Nc1cc2n(n1)CCc1c(-c3ccc(C)nc3)nn(-c3ccc(C4(N(C)C)CC4)cc3F)c1-2] | A-08 | [1-(3-fluoro-4-hydrazino-phenyl)-cyclopropyl]-dimethyl-amine | 486 | 1.63 |
| B-26 | 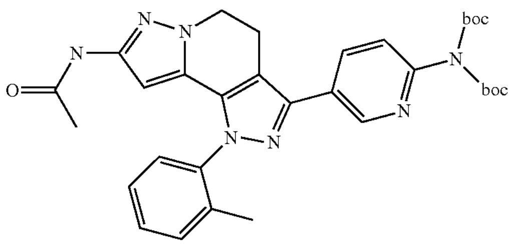 | A-09 | ortho-tolyl-hydrazine hydrochloride | 600 | 2.01 |
| B-27 | 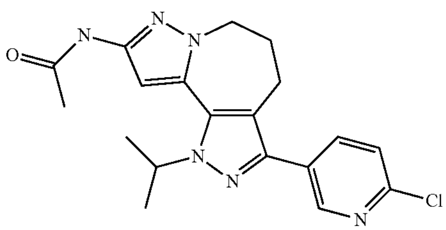 [SMILES: CC(=O)Nc1cc2n(n1)CCCc1c(-c3ccc(Cl)nc3)nn(C(C)C)c1-2] | A-10 | isopropyl-hydrazine hydrochloride | 385 | 1.69 |
| B-28 | 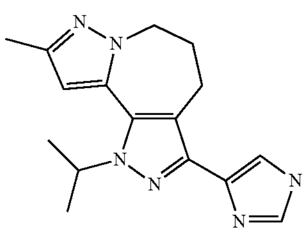 [SMILES: Cc1cc2n(n1)CCCc1c(-c3c[nH]cn3)nn(C(C)C)c1-2] | A-11 | isopropyl-hydrazine hydrochloride | 297 | 1.12 |
| B-29 | 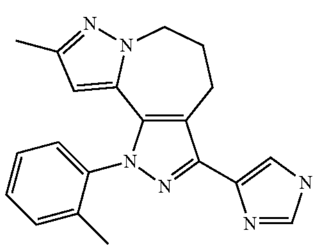 [SMILES: Cc1cc2n(n1)CCCc1c(-c3c[nH]cn3)nn(-c3ccccc3C)c1-2] | A-11 | ortho-tolyl-hydrazine hydrochloride | 345 | 1.21 |
| B-30 | 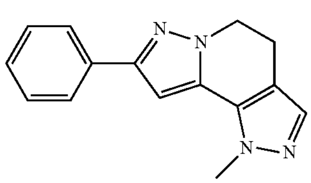 [SMILES: Cn1ncc2c1-c1cc(-c3ccccc3)nn1CC2] | A-12 | methyl-hydrazine hydrochloride | 251 | 1.39 |

TABLE 1-continued

Example B-01-B-32

| No. | Structure | Keto-ene-amine or 1,3-diketone | Hydrazine salt | M + H | R$_t$ (min) |
|---|---|---|---|---|---|
| B-31 | 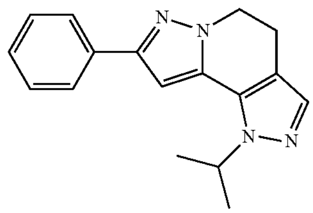 [SMILES: CC(C)n1ncc2c1-c1cc(-c3ccccc3)nn1CC2] | A-12 | isopropyl-hydrazine hydrochloride | 279 | 1.63 |
| B-32 | 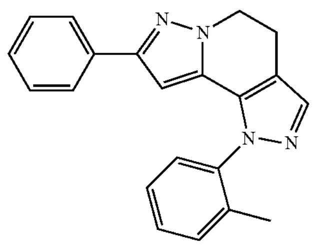 [SMILES: Cc1ccccc1-n1ncc2c1-c1cc(-c3ccccc3)nn1CC2] | A-12 | ortho-tolyl-hydrazine hydrochloride | 327 | 1.80 |

Examples C-01 to C-13 are synthesized according to general procedure C. The appropriate keto-ene-amine and amidine or guanidine required for synthesis can be deduced from the table of examples.

General Procedure C:

The appropriate keto-ene-amine (1 eq.) and the appropriate amidine- or guanidine salt (1-3 eq.) are taken up in pyridine and heated to 150° C. for 30 min using microwaves. The reaction mixture is cooled to RT, an aqueous saturated solution of NaHCO$_3$ is added and the reaction mixture is extracted with ethyl acetate. The combined organic phases are washed with water and brine, dried on MgSO$_4$ and the solvents are removed under reduced pressure. The product may be purified using NP or RP column chromatography.

TABLE 2

Example C-01-C-13

| No. | Structure | Keto-ene-amine | Amidine/Guanidine salt | M + H | R$_t$ (min) |
|---|---|---|---|---|---|
| C-01 | 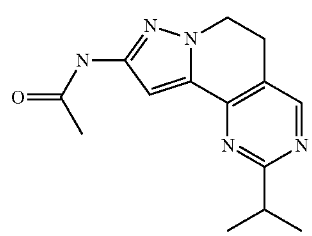 [SMILES: CC(=O)Nc1cc2n(n1)CCc1cnc(C(C)C)nc1-2] | A-01 | isopropyl-amidine hydrochloride | 272 | 1.17 |
| C-02 | 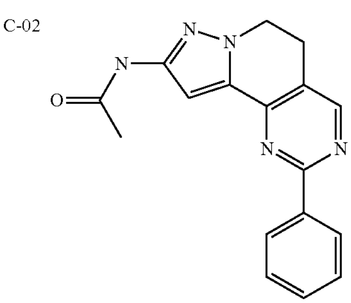 | A-01 | benzamidine hydrochloride | 306 | 1.46 |

TABLE 2-continued

Example C-01-C-13

| No. | Structure | Keto-ene-amine | Amidine/Guanidine salt | M + H | $R_t$ (min) |
|---|---|---|---|---|---|
| C-03 | | A-01 | N-ortho-tolyl-guanidine hydrochloride | 335 | 1.42 |
| C-04 | | A-01 | N-(2-methoxy-phenyl)-guanidine hydrochloride | 351 | 1.56 |
| C-05 | | A-02 | isopropyl-amidine hydrochloride | 286 | 1.29 |
| C-06 | | A-02 | benzamidine hydrochloride | 320 | 1.50 |
| C-07 | | A-02 | N-ortho-tolyl-guanidine hydrochloride | 349 | 1.48 |

TABLE 2-continued

Example C-01-C-13

| No. | Structure | Keto-ene-amine | Amidine/Guanidine salt | M + H | R$_t$ (min) |
|---|---|---|---|---|---|
| C-08 | 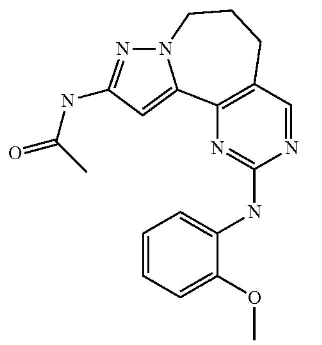 [SMILES: COc1ccccc1Nc1ncc2c(n1)-c1cc(NC(C)=O)nn1CCC2] | A-02 | N-(2-methoxy-phenyl)-guanidine hydrochloride | 365 | 1.61 |
| C-09 | 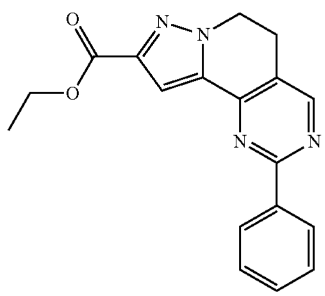 [SMILES: CCOC(=O)c1cc2n(n1)CCc1cnc(-c3ccccc3)nc1-2] | A-03 | benzamidine hydrochloride | 321 | |
| C-10 | 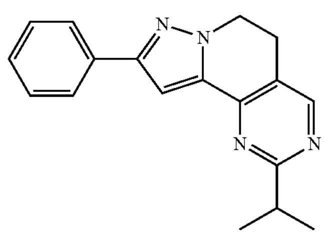 [SMILES: CC(C)c1ncc2c(n1)-c1cc(-c3ccccc3)nn1CC2] | A-12 | isopropyl-amidine hydrochloride | 291 | 1.75 |
| C-11 | 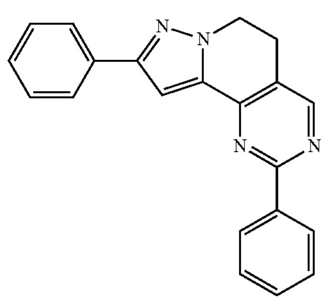 [SMILES: c1ccc(-c2cc3n(n2)CCc2cnc(-c4ccccc4)nc2-3)cc1] | A-12 | benzamidine hydrochloride | 325 | 1.97 |
| C-12 | 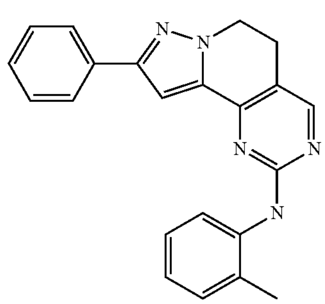 [SMILES: Cc1ccccc1Nc1ncc2c(n1)-c1cc(-c3ccccc3)nn1CC2] | A-12 | N-ortho-tolyl-guanidine hydrochloride | 354 | 1.89 |

TABLE 2-continued

Example C-01-C-13

| No. | Structure | Keto-ene-amine | Amidine/Guanidine salt | M + H | $R_t$ (min) |
|---|---|---|---|---|---|
| C-13 | 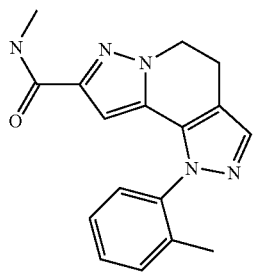 [SMILES: CNC(=O)c1cc2n(n1)CCc1cnn(-c3ccccc3C)c1-2] | A-12 | S-methylisothiourea | 295 | 1.70 |

Example D-01

1-o-Tolyl-4,5-dihydro-1H-1,2,5a,6-tetraaza-as-indacene-7-carboxylic acid methylamide

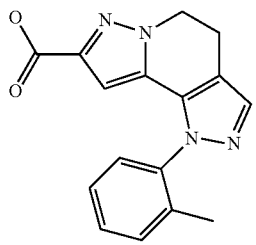 [SMILES: Cc1ccccc1-n1ncc2c1-c1cc(C(=O)O)nn1CC2]

D-01a) 1-o-Tolyl-4,5-dihydro-1H-1,2,5a,6-tetraaza-as-indacene-7-carboxylic acid

To a solution of B-07 (3.16 g, 9.80 mmol) in a mixture of 15 mL dioxane and 50 mL water is added LiOH (0.59 g, 25 mmol) and the reaction mixture is stirred for 2 days at RT. The reaction mixture is concentrated under reduced pressure and the crude product is used without further purification.

D-01a (0.50 g, 1.7 mmol) is suspended in 15 mL DMF, HATU (1.3 g, 3.4 mmol) and DIPEA (1.8 mL, 10 mmol) are added and the reaction mixture is stirred for 10 min at RT. A solution of methyl amine (2M in THF, 2.5 mL) is added and the reaction mixture is stirred over night at RT. Water is added and the reaction mixture is extracted with ethyl acetate. The combined organic phases are washed with brine, dried on $MgSO_4$ and the solvents are removed under reduced pressure. The residue is purified by flash column chromatography (silicagel, 0-70% ethyl acetate in cyclohexane). Yield: 0.35 g. HPLC-MS: $R_t$=1.99 min, $(M+H)^+$=308.

D-02) 8-Phenyl-4,5-dihydro-3,3a,7,9-tetraaza-benz[e]indene-2-carboxylic acid

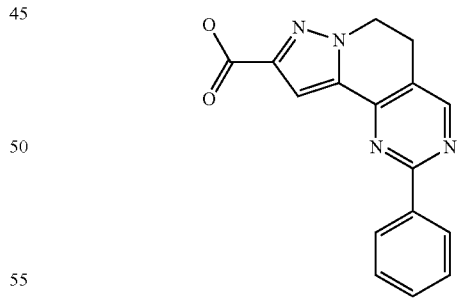

D-02 is prepared analogously to example D-01a from C-09. HPLC-MS: $R_t$=2.43 min, $(M+H)^+$=293.

Examples D-03 to D-26 are synthesized analogously to example D-01. The appropriate acid and amine required for synthesis can be deduced from the table of examples.

TABLE 3

| Example D-01-D-24 |||||||
|---|---|---|---|---|---|---|
| No. | Structure | | Acid | Amine | M + H | $R_t$ (min) |
| D-03 | | | D-01a | C-pyridin-3-yl-methylamine | 385 | 1.12 |
| D-04 | | | D-01a | pyridin-2-ylamine | 371 | 1.48 |
| D-05 | | | D-01a | C-pyridin-2-yl-methylamine | 385 | 1.22 |
| D-06 | | | D-01a | $N^1,N^1$-Dimethyl-propane-1,3-diamine | 379 | 1.49 |
| D-07 | | | D-01a | O-methyl-hydroxylamine | 324 | 0.96 |
| D-08 | | | D-01a | 3-methoxy-propylamine | 366 | 1.33 |

TABLE 3-continued

Example D-01-D-24

| No. | Structure | Acid | Amine | M + H | R$_t$ (min) |
|---|---|---|---|---|---|
| D-09 | 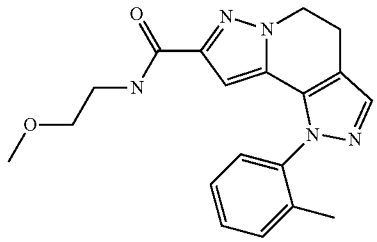 [SMILES: COCCNC(=O)c1cc2n(n1)CCc1cnn(-c3ccccc3C)c1-2] | D-01a | 2-methoxy-ethylamine | 352 | 1.27 |
| D-10 | 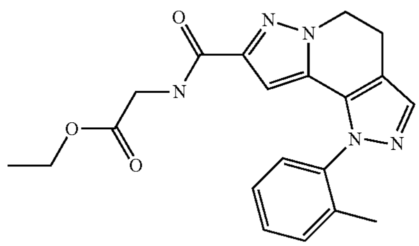 [SMILES: CCOC(=O)CNC(=O)c1cc2n(n1)CCc1cnn(-c3ccccc3C)c1-2] | D-01a | amino-acetic acid ethyl ester | 380 | 1.39 |
| D-11 | 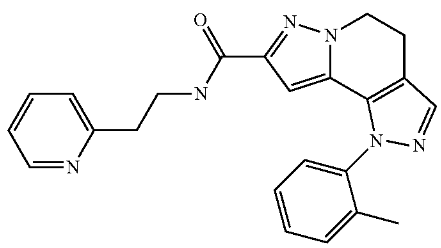 [SMILES: Cc1ccccc1-n1ncc2c1-c1cc(C(=O)NCCc3ccccn3)nn1CC2] | D-01a | 2-pyridin-2-yl-ethylamine | 399 | 1.35 |
| D-12 | 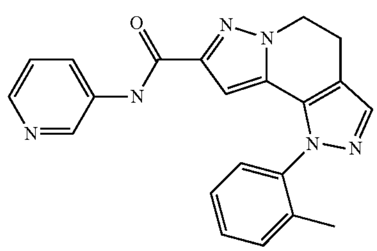 [SMILES: Cc1ccccc1-n1ncc2c1-c1cc(C(=O)Nc3cccnc3)nn1CC2] | D-01a | pyridin-3-ylamine | 371 | 1.36 |
| D-13 | 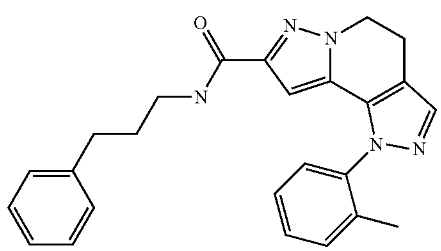 [SMILES: Cc1ccccc1-n1ncc2c1-c1cc(C(=O)NCCCc3ccccc3)nn1CC2] | D-01a | 3-phenyl-propylamine | 412 | 1.76 |
| D-14 | 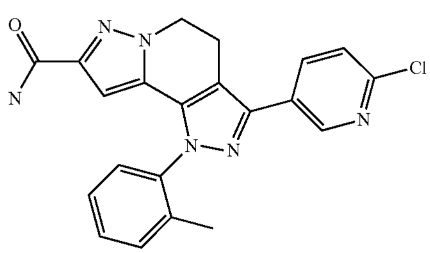 | B-22 | ammonium chloride | 405/407 | 1.68 |

TABLE 3-continued

Example D-01-D-24

| No. | Structure | Acid | Amine | M + H | R$_t$ (min) |
|---|---|---|---|---|---|
| D-15 | 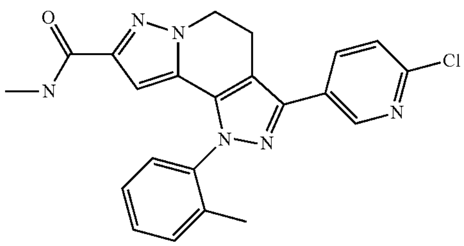 [SMILES: CNC(=O)c1cc2n(n1)CCc1c(-c3ccc(Cl)nc3)nn(-c3ccccc3C)c1-2] | B-22 | methylamine | 419/421 | 2.19 |
| D-16 | 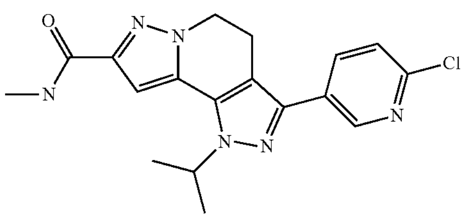 [SMILES: CNC(=O)c1cc2n(n1)CCc1c(-c3ccc(Cl)nc3)nn(C(C)C)c1-2] | B-23 | methylamine | 371/373 | 2.16 |
| D-17 | 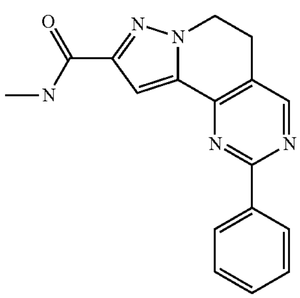 [SMILES: CNC(=O)c1cc2n(n1)CCc1cnc(-c3ccccc3)nc1-2] | D-02 | methylamine | 306 | 1.51 |
| D-18 | 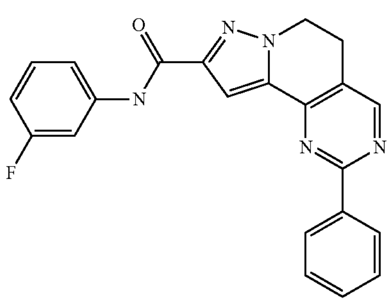 [SMILES: O=C(Nc1cccc(F)c1)c1cc2n(n1)CCc1cnc(-c3ccccc3)nc1-2] | D-02 | 3-fluorophenylamine | 386 | 1.84 |
| D-19 | 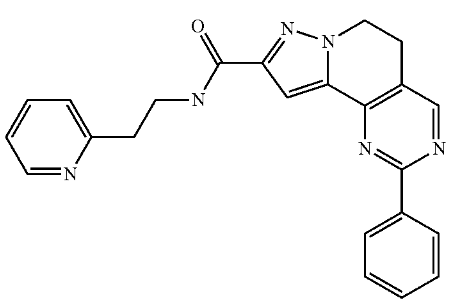 [SMILES: O=C(NCCc1ccccn1)c1cc2n(n1)CCc1cnc(-c3ccccc3)nc1-2] | D-02 | 2-pyridin-2-yl-ethylamine | 397 | 1.71 |

TABLE 3-continued

Example D-01-D-24

| No. | Structure | Acid | Amine | M + H | R$_t$ (min) |
|---|---|---|---|---|---|
| D-20 | 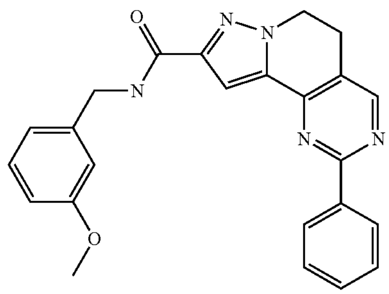 [SMILES: COc1cccc(CNC(=O)c2cc3n(n2)CCc2cnc(-c4ccccc4)nc2-3)c1] | D-02 | 3-methoxy-benzylamine | 412 | 1.69 |
| D-21 | 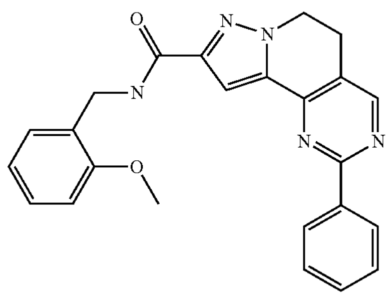 [SMILES: COc1ccccc1CNC(=O)c1cc2n(n1)CCc1cnc(-c3ccccc3)nc1-2] | D-02 | 2-methoxy-benzylamine | 412 | 1.74 |
| D-22 | 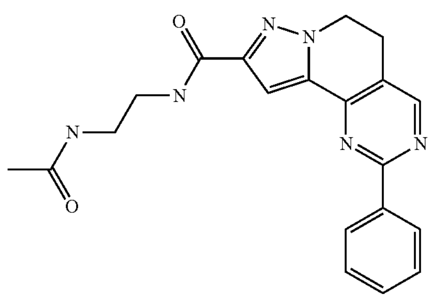 [SMILES: CC(=O)NCCNC(=O)c1cc2n(n1)CCc1cnc(-c3ccccc3)nc1-2] | D-02 | N-(2-amino-ethyl)-acetamide | 377 | 1.21 |
| D-23 | 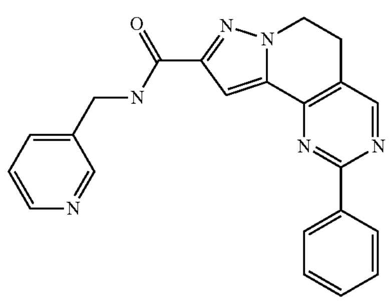 [SMILES: O=C(NCc1cccnc1)c1cc2n(n1)CCc1cnc(-c3ccccc3)nc1-2] | D-02 | C-pyridin-3-yl-methylamine | 383 | 1.38 |
| D-24 | 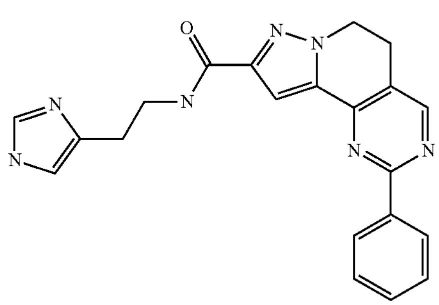 [SMILES: O=C(NCCc1c[nH]cn1)c1cc2n(n1)CCc1cnc(-c3ccccc3)nc1-2] | D-02 | 2-(1H-imidazol-4-yl)-ethylamine | 386 | 1.25 |

E-01) N-[3-(6-Amino-pyridin-3-yl)-1-isopropyl-4,5-dihydro-1H-1,2,5a,6-tetraaza-as-indacen-7-yl]-acetamide

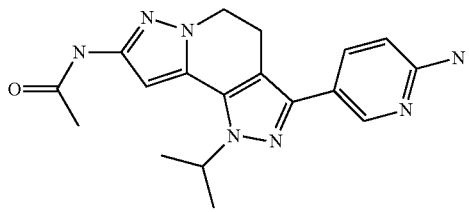 [SMILES: CC(=O)Nc1cc2n(n1)CCc1c(-c3ccc(N)nc3)nn(C(C)C)c1-2]

A mixture of B-17 (50 mg, 0.14 mmol), lithium bis(trimethylsilyl)amide (2 M in THF, 134 µL), 2-biphenyldicyclohexylphosphine (9.5 mg, 27 µmol) and tris(dibenzylideneacetone)dipalladium (12 mg, 13 µmol) is heated 10 min. at 120° C. using microwave irradiation. The reaction mixture is taken up in methanol and concentrated under reduced pressure. The residue is purified by RP HPLC (C18, 2-98% acetonitrile in water containg 0.1% formic acid). Yield: 16 mg. HPLC-MS: $R_t$=1.26 min, (M+H)$^+$=352.

Examples E-02 and E-03 are synthesized analogously to example E-01. The appropriate starting material required for synthesis can be deduced from the table of examples.

RP HPLC (C18, 7-50% acetonitrile in water containg 0.1% formic acid). Yield: 36 mg. HPLC-MS: $R_t$=1.37 min, (M+H)$^+$=309.

F-02) 3-(6-Amino-pyridin-3-yl)-1-o-tolyl-4,5-dihydro-1H-1,2,5a,6-tetraaza-as-indacen-7-ylamine

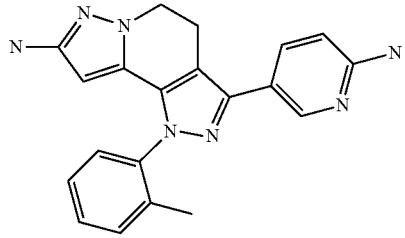

F-02 is prepared analogously to example F-01 starting from B-26. HPLC-MS: $R_t$=1.18 min, (M+H)$^+$=358.

TABLE 1

| No. | Structure | Starting material | M + H | $R_t$ (min) |
|---|---|---|---|---|
| E-02 | 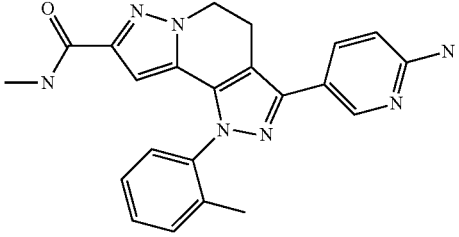 [SMILES: CNC(=O)c1cc2n(n1)CCc1c(-c3ccc(N)nc3)nn(-c3ccccc3C)c1-2] | D-17 | 400 | 1.39 |
| E-03 | 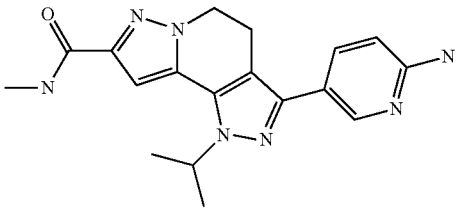 [SMILES: CNC(=O)c1cc2n(n1)CCc1c(-c3ccc(N)nc3)nn(C(C)C)c1-2] | D-18 | 352 | 1.27 |

F-01) 1-Isopropyl-3-(6-methyl-pyridin-3-yl)-4,5-dihydro-1H-1,2,5a,6-tetraaza-as-indacen-7-ylamine

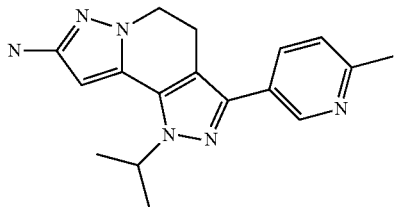 [SMILES: Cc1ccc(-c2nn(C(C)C)c3c2CCn2nc(N)cc2-3)cn1]

B-24 (0.24 g, 0.68 mmol) is taken up in 5 mL dioxane, 0.54 mL concentrated HCl is added and the reaction mixture is stirred at 80° C. for 0.5 h. The reaction mixture is concentrated under reduced pressure and the residue is purified by G-01) [3-(6-Chloro-pyridin-3-yl)-1-o-tolyl-4,5-dihydro-1H-1,2,5a,6-tetraaza-as-indacen-7-yl]-methanol

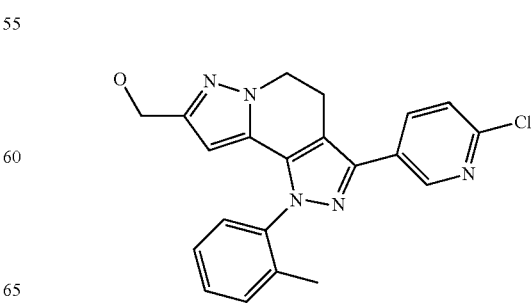

B-22 (0.82 g, 2.0 mmol) is taken up in 28 mL dry THF, the reaction mixture is cooled to 0° C., borane-THF complex (1 M in THF, 14 mL) is added and the reaction mixture is stirred overnight while warming up to RT. The reaction mixture is cooled to 0° C. and 5 mL water is added. The cooling bath is removed and the reaction mixture is stirred at RT for 0.5 h. The reaction mixture is extracted with DCM, the combined organic phases are dried over MgSO$_4$ and concentrated under reduced pressure. The residue is purified by flash column chromatography (silicagel, 0-5% isopropanol in ethyl acetate). Yield: 0.38 g. HPLC-MS: R$_t$=1.67 min, (M+H)$^+$=392/394.

G-02) 7-Chloromethyl-3-(6-chloro-pyridin-3-yl)-1-o-tolyl-4,5-dihydro-1H-1,2,5a,6-tetraaza-as-indacene

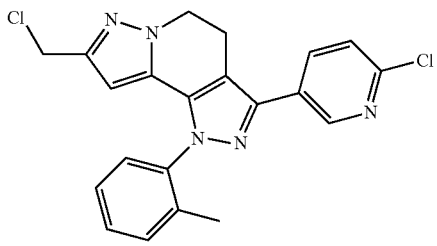 [SMILES: Cc1ccccc1-n1nc(-c2ccc(Cl)nc2)c2c1-c1cc(CCl)nn1CC2]

G-01 (0.38 g, 0.97 mmol) is taken up in 4 mL DCM, thionyl chloride (0.14 mL, 1.9 mmol) is added and the reaction mixture is stirred at RT for 1 h. The reaction mixture is concentrated under reduced pressure and the residual product is used in the next without further purification. Yield: 0.43 g. HPLC-MS: R$_t$=2.66 min, (M+H)$^+$=410/412.

G-03) [3-(6-Chloro-pyridin-3-yl)-1-o-tolyl-4,5-dihydro-1H-1,2,5a,6-tetraaza-as-indacen-7-yl]-acetonitrile

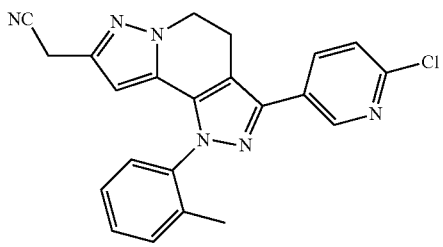 [SMILES: Cc1ccccc1-n1nc(-c2ccc(Cl)nc2)c2c1-c1cc(CC#N)nn1CC2]

G-02 (140 mg, 341 µmol) is taken up in 1 mL DMSO, sodium cyanate (50 mg, 1.0 mmol) is added and the reaction mixture is stirred at RT for 2 h. The product is purified by RP HPLC (C18, 50-98% methanol in water containing 0.1% formic acid). Yield: 64 mg. HPLC-MS: R$_t$=1.91 min, (M+H)$^+$=401/403.

G-04) [3-(6-Chloro-pyridin-3-yl)-1-o-tolyl-4,5-dihydro-1H-1,2,5a,6-tetraaza-as-indacen-7-ylmethyl]-methyl-amine

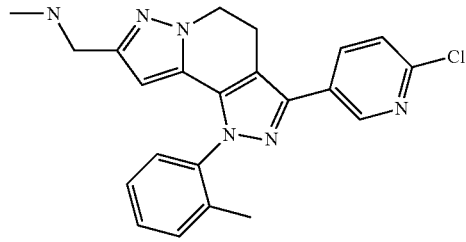 [SMILES: CNCc1cc2n(n1)CCc1c(-c3ccc(Cl)nc3)nn(-c3ccccc3C)c1-2]

G-02 (177 mg, 431 mmol) is taken up in 1 mL DMSO, methylamine (2 M in THF, 1.1 mL) is added and the reaction mixture is stirred at RT for 1 h. The product is purified by RP HPLC (C18, 50-98% methanol in water containing 0.1% formic acid). Yield: 28 mg. HPLC-MS: R$_t$=1.96 min, (M+H)$^+$=405/407.

G-05) 3-(6-Chloro-pyridin-3-yl)-7-methyl-1-o-tolyl-4,5-dihydro-1H-1,2,5a,6-tetraaza-as-indacene

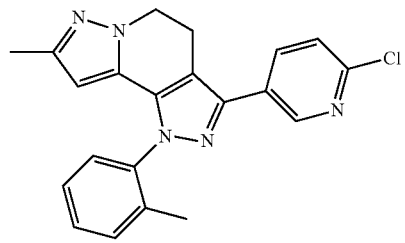 [SMILES: Cc1cc2n(n1)CCc1c(-c3ccc(Cl)nc3)nn(-c3ccccc3C)c1-2]

G-02 (140 mg, 341 µmol) is taken up in 15 mL methanol, palladium on carbon (5%, 60 mg) is added and the reaction mixture is stirred at RT for 2 h under 5 bar dihydrogen. The reaction mixture is filtered over Celite, concentrated under reduced pressure and the residue is purified by RP HPLC (C18, 40-98% methanol in water containing 0.1% formic acid). Yield: 8.7 mg. HPLC-MS: R$_t$=1.94 min, (M+H)$^-$=376/378.

G-06) 3-(6-Chloro-pyridin-3-yl)-1-o-tolyl-4,5-dihydro-1H-1,2,5a,6-tetraaza-as-indacene-7-carbonitrile

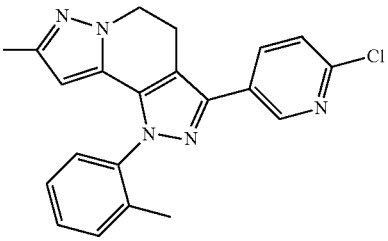

D-16 (50 mg, 124 µmol) is taken up in 1 mL phosphorus oxychloride, phosphorus pentachloride (97 mg, 469 µmol) is added and the reaction mixture is heated 10 min. at 120° C. using microwave irradiation. The reaction mixture is dropped in 15 mL ice-water and the reaction mixture is extracted with dichloromethane. The combined organic phases are dried over $MgSO_4$ and concentrated under reduced pressure. The residue is purified by RP HPLC (C18, 50-98% methanol in water containing 0.1% formic acid). Yield: 20 mg. HPLC-MS: $R_t$=2.07 min, $(M+H)^+$=387/389.

Additionally, the following compounds can be prepared according to methods described herein or in WO2006/040279.

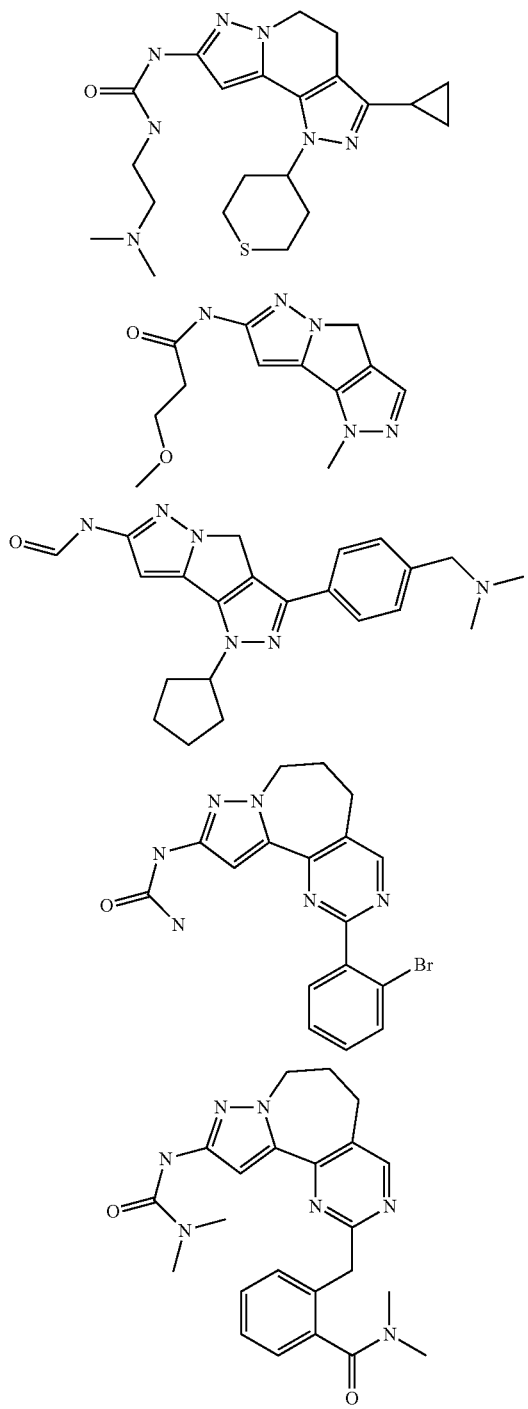

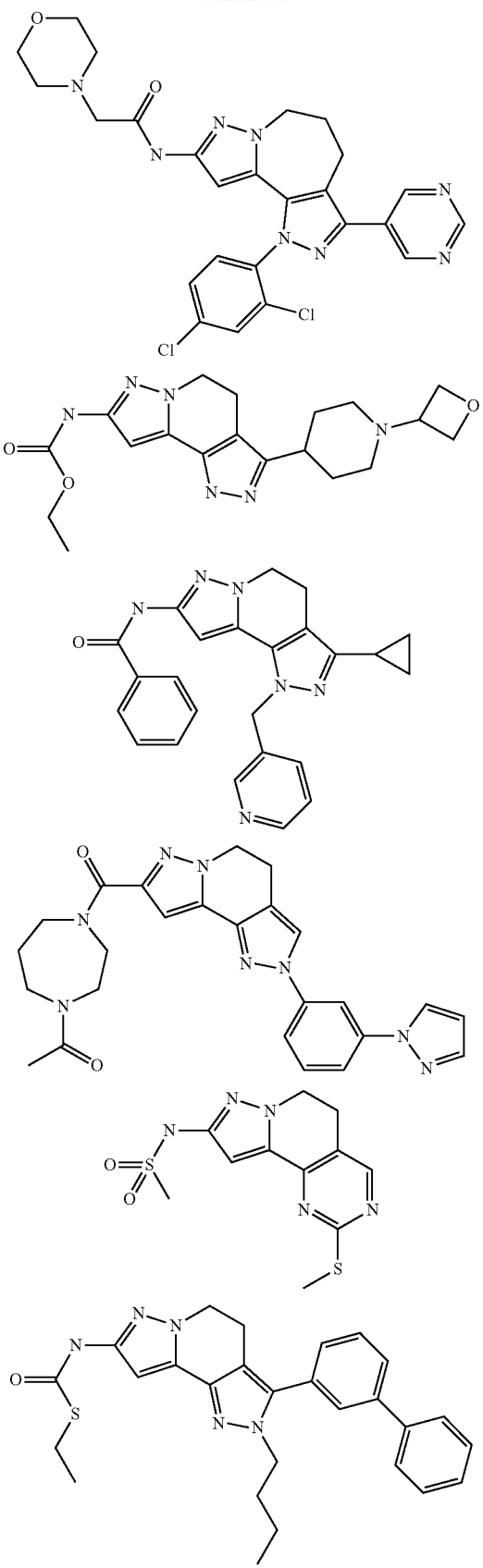

-continued

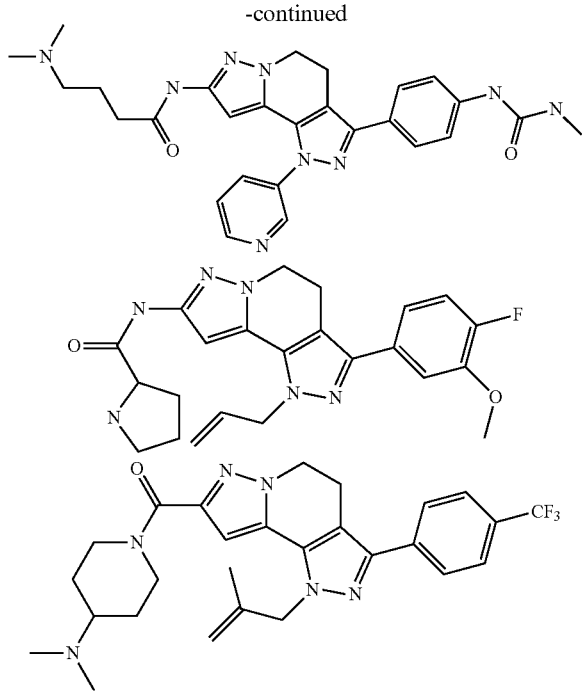

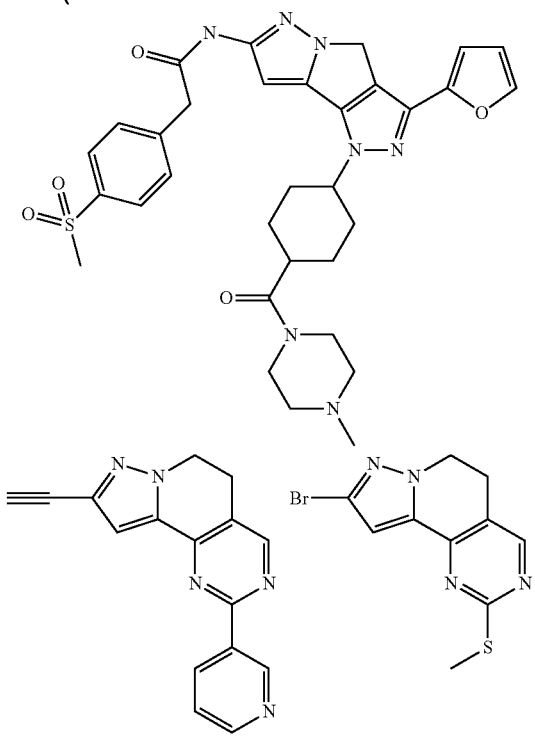

Analytical Method 1

| HPLC: | Agilent 1100 Series |
|---|---|
| MS: | Agilent LC/MSD SL |
| column: | Phenomenex, Mercury Gemini C18, 3 μm, 2.0 × 20 mm |
| solvent | A: 5 mM $NH_4HCO_3$/20 mM $NH_3$ |
| | B: acetonitrile HPLC grade |
| detection: | MS: Positive and negative |
| | mass range: 120-700 m/z |
| | fragmentor: 70 |
| | gain EMV: 1 |
| | threshold: 150 |
| | stepsize: 0.25 |
| | UV: 315 nm |
| | bandwidth: 170 nm |
| | reference: off |
| | range: 210-400 nm |
| | range step: 2.00 nm |
| | peakwidth: <0.01 min |
| | slit: 2 nm |
| injection: | 5 μL |
| flow: | 1.00 mL/min |
| column temperature: | 40° C. |
| gradient: | 0.00 min   5% B |
| | 0.00-2.50 min   5% → 95% B |
| | 2.50-2.80 min   95% B |
| | 2.81-3.10 min   95% → 5% B |

Analytical Method 2

| HPLC: | Agilent 1100/1200 Series |
|---|---|
| MS: | Agilent LC/MSD SL |
| column: | Waters, Sunfire, C18, 5 μm, 2.1 × 50 mm |
| solvent | A: $H_2O$ + 0.1% formic acid |
| | B: acetonitrile HPLC grade + 0.1% formic acid |
| detection: | MS: Positive and negative |
| mass range: | 100-750 m/z |
| | fragmentor: 70 |
| | gain EMV: 1 |
| | threshold: 150 |
| | stepsize: 0.30 |
| | UV: 254/210 nm |
| | bandwidth: 8 nm |
| | reference: off |
| | range: 190-400 nm |
| | range step: 4.00 nm |
| | peakwidth: <0.01 min |
| | slit: 4 nm |
| injection: | 1-5 μL |
| flow: | 1.00 mL/min |
| column temperature: | 40° C. |
| gradient: | 0.00-0.10 min   5% B |
| | 0.10-1.50 min   5% → 95% B |
| | 1.50-2.10 min   95% B |
| | 2.10-2.20 min   95% → 5% B |

Abbreviations Used

| ACN | acetonitrile |
|---|---|
| BOC | tert-butoxy-carbonyl |
| CDI | carbonyl diimidazole |
| conc. | concentrated |
| d | day(s) |
| DBU | 1,8-diazabicyclo[5.4.0]undec-7-ene |
| DCE | 1,2-dichloroethane |
| DCM | dichloromethan |
| DIPEA | diisopropylethyl amine |
| DMA | N,N-dimethylacetamide |
| DMAP | dimethyl-pyridin-4-yl-amine |
| DMF | N,N-dimethylformamide |

| | -continued |
|---|---|
| DMSO | dimethylsulphoxide |
| EtOH | ethanol |
| h | hour(s) |
| HATU | N-[(dimethylamino)-(1H-1,2,3-triazolo[4,5-b]pyridin-1-yl)-methylene[-N-methylmethan-aminium hexafluorophosphate N-oxide |
| HPLC | high performance liquid chromatography |
| iPr | isopropyl |
| LHMDS | lithium hexamethyl disilazide |
| M | molar |
| min | minute(s) |
| mL | millilitre |
| μL | microlitre |
| mm | millimeter |
| m.p. | melting point |
| MS | mass spectrometry |
| MTBE | methyl-tert-butylether |
| N | normal |
| nm | nanometer |
| μm | micrometer |
| NMP | N-methylpyrrolindinone |
| NMR | nuclear resonance spectroscopy |
| NP | normal phase |
| ppm | part per million |
| RP | reversed phase |
| RT | room temperature |
| $R_t$ | retention time |
| tert | tertiary |
| THF | tetrahydrofuran |

The Examples that follow describe the biological activity of the compounds according to the invention without restricting the invention to these Examples.

PC3 Proliferation Test

The test is based on measurement of cellular DNA content via fluorescent dye binding. Because cellular DNA content is highly regulated, it is closely proportional to cell number. The extent of proliferation is determined by comparing cell counts for samples treated with drugs with untreated controls.

PC3 (human prostate carcinoma cell line) cells are sown in microtitre plates and incubated overnight in culture medium at 37° C. and 5% $CO_2$. The test substances are diluted stepwise and added to the cells such that the total volume is 200 μL/well. Cells to which diluent, but not substance, is added serve as controls. After an incubation time of 3 days, the medium is replaced by 100 μL/well dye-binding solution and the cells are incubated at 37° C. in the dark for a further 60 min. For measuring the fluorescence, excitation takes place at a wavelength of 485 nm and the emission is measured at 530 nm.

$EC_{50}$ values are calculated using the GraphPad Prism program.

Most compounds of the Examples cited have an $EC_{50}$ (Proliferation PC3) of less than 10 μM.

P-AKT Measurement in PC3 Cells

P-AKT levels in PC3 cells are detected by cell-based ELISA. Cells are cultured in 96-well plates and treated with serial dilutions of test substances for 2 h. Cells to which diluent, but not substance, is added serve as controls. Subsequently, the cells are fixed rapidly to preserve protein modifications. Each well is then incubated with a primary antibody specific for Ser473-phosphorylated AKT. Subsequent incubation with secondary HRP-conjugated antibody and developing solution provides a colorimetric readout at 450 nm. $EC_{50}$ values are calculated using the GraphPad Prism program.

Most compounds of the Examples cited have an $EC_{50}$ (P-AKT PC3) of less than 10 μM.

The substances of the present invention are PI3 kinase inhibitors. On account of their biological properties, the novel compounds of the general formula (1) and their isomers and their physiologically tolerated salts are suitable for treating diseases which are characterized by excessive or anomalous cell proliferation.

These diseases include, for example: viral infections (e.g. HIV and Kaposi's sarcoma); inflammation and autoimmune diseases (e.g. colitis, arthritis, Alzheimer's disease, glomerulonephritis and wound healing); bacterial, fungal and/or parasitic infections; leukaemias, lymphomas and solid tumours; skin diseases (e.g. psoriasis); bone diseases; cardiovascular diseases (e.g. restenosis and hypertrophy). In addition, the compounds are useful for protecting proliferating cells (e.g. hair cells, intestinal cells, blood cells and progenitor cells) from DNA damage due to irradiation, UV treatment and/or cytostatic treatment (Davis et al., 2001).

For example, the following cancer diseases can be treated with compounds according to the invention, without, however, being restricted thereto: brain tumours, such as acoustic neurinoma, astrocytomas such as piloid astrocytomas, fibrillary astrocytoma, protoplasmic astrocytoma, gemistocytic astrocytoma, anaplastic astrocytoma and glioblastomas, brain lymphomas, brain metastases, hypophyseal tumour such as prolactinoma, HGH (human growth hormone) producing tumour and ACTH-producing tumour (adrenocorticotrophic hormone), craniopharyngiomas, medulloblastomas, meningiomas and oligodendrogliomas; nerve tumours (neoplasms) such as tumours of the vegetative nervous system such as neuroblastoma sympathicum, ganglioneuroma, paraganglioma (phaeochromocytoma and chromaffinoma) and glomus caroticum tumour, tumours in the peripheral nervous system such as amputation neuroma, neurofibroma, neurinoma (neurilemoma, schwannoma) and malignant schwannoma, as well as tumours in the central nervous system such as brain and spinal cord tumours; intestinal cancer such as rectal carcinoma, colon carcinoma, anal carcinoma, small intestine tumours and duodenal tumours; eyelid tumours such as basalioma or basal cell carcinoma; pancreatic gland cancer or pancreatic carcinoma; bladder cancer or bladder carcinoma; lung cancer (bronchial carcinoma) such as small-cell bronchial carcinomas (oat cell carcinomas) and non-small-cell bronchial carcinomas such as squamous epithelium carcinomas, adenocarcinomas and large-cell bronchial carcinomas; breast cancer such as mammary carcinoma, such as infiltrating ductal carcinoma, colloid carcinoma, lobular invasive carcinoma, tubular carcinoma, adenoid cystic carcinoma, and papillary carcinoma; non-Hodgkin's lymphomas (NHL) such as Burkitt's lymphoma, low-malignancy non-Hodkgin's lymphomas (NHL) and mucosis fungoides; uterine cancer or endometrial carcinoma or corpus carcinoma; CUP syndrome (cancer of unknown primary); ovarian cancer or ovarian carcinoma such as mucinous, endometrial or serous cancer; gall bladder cancer; bile duct cancer such as Klatskin's tumour; testicular cancer such as seminomas and non-seminomas; lymphoma (lymphosarcoma) such as malignant lymphoma, Hodgkin's disease, non-Hodgkin's lymphomas (NHL) such as chronic lymphatic leukaemia, hair cell leukaemia, immunocytoma, plasmocytoma (multiple myeloma), immunoblastoma, Burkitt's lymphoma, T-zone mycosis fungoides, large-cell anaplastic lymphoblastoma and lymphoblastoma; laryngeal cancer such as vocal cord tumours, supraglottal, glottal and subglottal laryngeal tumours; bone cancer such as osteochondroma, chondroma, chrondoblastoma, chondromyxoidfibroma, osteoma, osteoid-osteoma, osteoblastoma, eosinophilic granuloma, giant cell tumour, chondrosarcoma, osteosarcoma, Ewing's sarcoma, reticulo sarcoma, plasmocytoma, fibrous dysplasia, juvenile bone cyst and aneurysmatic bone cyst; head/neck tumours such as tumours of the lips, tongue, floor of the mouth, oral cavity, gingiva, pallet, salivary glands, pharynx, nasal cavities, paranasal sinuses, larynx and middle ear; liver cancer such as liver cell carcinoma or hepatocellular carcinoma (HCC); leukaemias, such as acute leukaemias, such as acute lymphatic/lymphoblastic leukaemia (ALL), acute myeloid leukaemia (AML); chronic leukaemias such as chronic lymphatic leukaemia (CLL), chronic myeloid leukaemia (CML); stomach cancer or stomach carcinoma such as papillary, tubular and mucinous adenocarcinoma, signet ring cell carcinoma, adenoid squamous cell carcinoma, small-cell carcinoma and undifferentiated carcinoma; melanomas such as superficially spreading, nodular malignant lentigo and acral lentiginous melanoma; renal cancer, such as kidney cell carcinoma or hypernephroma or Grawitz's tumour; oesophageal cancer or oesophageal carcinoma; cancer of the penis; prostate cancer; pharyngeal cancer or pharyngeal carcinomas such as nasopharyngeal carcinomas, oropharyngeal carcinomas and hypopharyngeal carcinomas; retinoblastoma; vaginal cancer or vaginal carcinoma; squamous epithelium carcinomas, adeno carcinomas, in situ carcinomas, malignant melanomas and sarcomas; thyroid gland carcinomas such as papillary, follicular and medullary thyroid gland carcinoma, and also anaplastic carcinomas; spinalioma, prickle cell carcinoma and squamous epithelium carcinoma of the skin; thymomas, urethral cancer and vulvar cancer.

The novel compounds can be used for the prevention or short-term or long-term treatment of the abovementioned diseases including, where appropriate, in combination with other state-of-the-art compounds such as other anti-tumour substances, cytotoxic substances, cell proliferation inhibitors, antiangiogenic substances, steroids or antibodies.

The compounds of the general formula (1) can be used on their own or in combination with other active compounds according to the invention and, where appropriate, in combination with other pharmacologically active compounds as well. Chemotherapeutic agents which can be administered in combination with the compounds according to the invention include, without being restricted thereto, hormones, hormone analogs and antihormones (e.g. tamoxifen, toremifene, raloxifene, fulvestrant, megestrol acetate, flutamide, nilutamide, bicalutamide, aminoglutethimide, cyproterone acetate, finasteride, buserelin acetate, fludrocortisone, fluoxymesterone, medroxyprogesterone and octreotide), aromatase inhibitors (e.g. anastrozole, letrozole, liarozole, vorozole, exemestane and atamestane), LHRH agonists and antagonists (e.g. goserelin acetate and luprolide), inhibitors of growth factors (growth factors such as platelet-derived growth factor and hepatocyte growth factor, examples of inhibitors are growth factor antibodies, growth factor receptor antibodies and tyrosine kinase inhibitors, such as gefitinib, imatinib, lapatinib, Erbitux® and trastuzumab); antimetabolites (e.g. antifolates such as methotrexate and raltitrexed, pyrimidine analogs such as 5-fluorouracil, capecitabine and gemcitabine, purine and adenosine analogs such as mercaptopurine, thioguanine, cladribine and pentostatin, cytarabine and fludarabine); antitumour antibiotics (e.g. anthracyclines, such as doxorubicin, daunorubicin, epirubicin and idarubicin, mitomycin C, bleomycin, dactinomycin, plicamycin and streptozocin); platinum derivatives (e.g. cisplatin, oxaliplatin and carboplatin); alkylating agents (e.g. estramustine, meclorethamine, melphalan, chlorambucil, busulphan, dacarbazine, cyclophosphamide, ifosfamide and temozolomide, nitrosoureas such as carmustine and lomustine and thiotepa);

antimitotic agents (e.g. vinca alkaloids such as vinblastine, vindesine, vinorelbine and vincristine; and taxans such as paclitaxel and docetaxel); topoisomerase inhibitors (e.g. epipodophyllotoxins such as etoposide and etopophos, teniposide, amsacrine, topotecan, irinotecan and mitoxantrone) and various chemotherapeutic agents such as amifostin, anagrelide, clodronate, filgrastin, interferon alpha, leucovorin, rituximab, procarbazine, levamisole, mesna, mitotan, pamidronate and porfimer.

Examples of suitable forms for use are tablets, capsules, suppositories, solutions, in particular solutions for injection (s.c., i.v., i.m.) and infusion, syrups, emulsions or dispersible powders. In this connection, the proportion of the pharmaceutically active compound(s) should in each case be in the range of 0.1-90% by weight, preferably 0.5-50% by weight, of the total composition, that is in quantities which are sufficient to achieve the dosage range which is specified below. If necessary, the doses mentioned can be given several times a day.

Appropriate tablets can be obtained, for example, by mixing the active compound(s) with known auxiliary substances, for example inert diluents, such as calcium carbonate, calcium phosphate or lactose, disintegrants, such as maize starch or alginic acid, binders, such as starch or gelatine, lubricants, such as magnesium stearate or talc, and/or agents for achieving a depot effect, such as carboxymethyl cellulose, cellulose acetate phthalate or polyvinyl acetate. The tablets can also comprise several layers.

Correspondingly, sugar-coated tablets can be produced by coating cores, which have been prepared in analogy with tablets, with agents which are customarily used in sugar coatings, for example collidone or shellac, gum arabic, talc, titanium dioxide or sugar. The core can also comprise several layers in order to achieve a depot effect or to avoid incompatibilities.

In the same way, the sugar coating can also comprise several layers in order to achieve a depot effect, with it being possible to use the auxiliary substances which are mentioned above in the case of the tablets.

Syrups of the active compounds or active compound combinations according to the invention can additionally comprise a sweetening agent, such as saccharine, cyclamate, glycerol or sugar as well as a taste-improving agent, e.g. flavouring agents such as vanillin or orange extract. They can also comprise suspension aids or thickeners, such as sodium carboxymethyl cellulose, wetting agents, for example condensation products of fatty alcohols and ethylene oxide, or protectants such as p-hydroxybenzoates.

Injection and infusion solutions are produced in a customary manner, e.g. while adding isotonizing agents, preservatives, such as p-hydroxybenzoates, or stabilizers, such as alkali metal salts of ethylenediaminetetraacetic acid, where appropriate using emulsifiers and/or dispersants, with it being possible, for example, to employ, where appropriate, organic solvents as solubilizing agents or auxiliary solvents when using water as diluent, and aliquoted into injection bottles or ampoules or infusion bottles.

The capsules, which comprise one or more active compounds or active compound combinations, can, for example, be produced by mixing the active compounds with inert carriers, such as lactose or sorbitol, and encapsulating the mixture in gelatine capsules. Suitable suppositories can be produced, for example, by mixing with excipients which are envisaged for this purpose, such as neutral fats or polyethylene glycol, or their derivatives.

Auxiliary substances which may be mentioned by way of example are water, pharmaceutically unobjectionable organic solvents, such as paraffins (e.g. petroleum fractions), oils of vegetable origin (e.g. groundnut oil or sesame oil), monofunctional or polyfunctional alcohols (e.g. EtOH or glycerol), carrier substances such as natural mineral powders (e.g. kaolins, argillaceous earths, talc and chalk), synthetic mineral powders (e.g. highly disperse silicic acid and silicates), sugars (e.g. cane sugar, lactose and grape sugar), emulsifiers (e.g. lignin, sulphite waste liquors, methyl cellulose, starch and polyvinylpyrrolidone) and glidants (e.g. magnesium stearate, talc, stearic acid and sodium lauryl sulphate).

Administration is effected in a customary manner, preferably orally or transdermally, in particular and preferably orally. In the case of oral use, the tablets can naturally also comprise, in addition to the abovementioned carrier substances, additives such as sodium citrate, calcium carbonate and dicalcium phosphate together with a variety of further substances such as starch, preferably potato starch, gelatine and the like. It is furthermore also possible to use glidants, such as magnesium stearate, sodium lauryl sulphate and talc, for the tableting. In the case of aqueous suspensions, a variety of taste improvers or dyes can also be added to the active compounds in addition to the abovementioned auxiliary substances.

For parenteral administration, it is possible to employ solutions of the active compounds while using suitable liquid carrier materials. The dosage for intravenous administration is 1-1000 mg per hour, preferably between 5 and 500 mg per hour.

Despite this, it may be necessary, where appropriate, to diverge from the abovementioned quantities, depending on the body weight or the nature of the route of administration, on the individual response to the medicament, on the nature of its formulation and on the time or interval at which the administration is effected. Thus, it may, in some cases, be sufficient to make do with less than the previously mentioned lowest quantity whereas, in other cases, the abovementioned upper limit has to be exceeded. When relatively large quantities are being administered, it may be advisable to divide these into several single doses which are given over the course of the day.

The following formulation examples illustrate the present invention without, however, restricting its scope:

Pharmaceutical Formulation Examples

| A) Tablets | per tablet |
|---|---|
| Active compound in accordance with formula (1) | 100 mg |
| Lactose | 140 mg |
| Maize starch | 240 mg |
| Polyvinylpyrrolidone | 15 mg |
| Magnesium stearate | 5 mg |
| | 500 mg |

The finely ground active compound, lactose and a part of the maize starch are mixed with each other. The mixture is sieved, after which it is moistened with a solution of polyvinylpyrrolidone in water, kneaded, wet-granulated and dried. The granular material, the remainder of the maize starch and the magnesium stearate are sieved and mixed with each other. The mixture is pressed into tablets of suitable shape and size.

| B) Tablets | per tablet |
|---|---|
| Active compound in accordance with formula (1) | 80 mg |
| Lactose | 55 mg |
| Maize starch | 190 mg |
| Microcrystalline cellulose | 35 mg |
| Polyvinylpyrrolidone | 15 mg |
| Sodium carboxymethyl starch | 23 mg |
| Magnesium stearate | 2 mg |
| | 400 mg |

The finely ground active compound, a part of the maize starch, the lactose, microcrystalline cellulose and polyvinylpyrrolidone are mixed with each other, after which the mixture is sieved and worked, together with the remainder of the maize starch and water, into a granular material, which is dried and sieved. The sodium carboxymethyl starch and the magnesium stearate are then added to the granular material and mixed with it, and the mixture is pressed into tablets of suitable size.

| C) Ampoule solution | |
|---|---|
| Active compound in accordance with formula (1) | 50 mg |
| Sodium chloride | 50 mg |
| Water for injection | 5 ml |

The active compound is dissolved, either at its intrinsic pH or, where appropriate, at pH 5.5-6.5, in water after which sodium chloride is added as isotonizing agent. The resulting solution is rendered pyrogen-free by filtration and the filtrate is aliquoted, under aseptic conditions, into ampoules, which are then sterilized and sealed by melting. The ampoules contain 5 mg, 25 mg and 50 mg of active compound.

The invention claimed is:
1. A compound of formula (I),

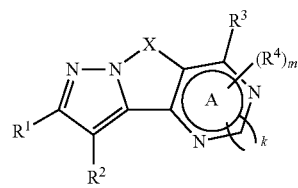

wherein
$R^1$, $R^2$, $R^3$ and $R^4$ independently of one another denote $R^5$; and
A denotes an aromatic ring; and
X is an optionally substituted $C_2$-$C_3$ alkylidene chain; and
m is 1;
k is 0; and
each $R^5$ denotes a group selected from among $R^a$, $R^b$ and $R^a$ substituted by one or more identical or different $R^b$ and/or $R^c$; and
each $R^a$ independently of one another denotes hydrogen or a group optionally substituted by one or more identical or different $R^b$ and/or $R^c$, selected from among $C_{1-6}$alkyl, 2-6 membered heteroalkyl, $C_{1-6}$haloalkyl, $C_{3-10}$Cycloalkyl, $C_{4-16}$Cycloalkylalkyl, $C_{6-10}$-aryl, $C_{7-16}$arylalkyl, 5-12 membered heteroaryl, 6-18 membered heteroarylalkyl, 3-14 membered heterocycloalkyl and 4-14 membered heterocycloalkylalkyl, each $R^b$ denotes a suitable group and is selected independently of one another from among =O, —$OR^c$, $C_{1-3}$haloalkyloxy, —$OCF_3$, =S, —$SR^c$, =$NR^c$, =$NOR^c$, =$NNR^cR^c$, =$NN(R^g)C(O)NR^cR^c$, —$NR^cR^c$, —$ONR^cR^c$, —$N(OR^c)R^c$, —$N(R^g)NR^cR^c$, halogen, —$CF_3$, —CN, —NC, —OCN, —SCN, —NO, —$NO_2$, =$N_2$, —$N_3$, —$S(O)R^c$, —$S(O)OR^c$, —$S(O)_2R^c$, —$S(O)_2OR^c$, —$S(O)NR^cR^c$, —$S(O)_2NR^cR^c$, —$OS(O)R^c$, —$OS(O)_2R^c$, —$OS(O)_2OR^c$, —$OS(O)NR^cR^c$, —$OS(O)_2NR^cR^c$, —$C(O)R^c$, —$C(O)OR^c$, —$C(O)SR^c$, —$C(O)NR^cR^c$, —$C(O)N(R^g)NR^cR^c$, —$C(O)N(R^g)OR^c$, —$C(NR^g)NR^cR^c$, —$C(NOH)R^c$, —$C(NOH)NR^cR^c$, —$OC(O)R^c$, —$OC(O)OR^c$, —$OC(O)SR^c$, —$OC(O)NR^cR^c$, —$OC(NR^g)NR^cR^c$, —$SC(O)R^c$, —$SC(O)OR^c$, —$SC(O)NR^cR^c$, —$SC(NR^g)NR^cR^c$, —$N(R^g)C(O)R^c$, —$N[C(O)R^c]_2$, —$N(OR^g)C(O)R^c$, —$N(R^g)C(NR^g)R^c$, —$N(R^g)N(R^g)C(O)R^c$, —$N[C(O)R^c]NR^cR^c$, —$N(R^g)C(S)R^c$, —$N(R^g)S(O)R^c$, —$N(R^g)S(O)OR^c$, —$N(R^g)S(O)_2R^c$, —$N[S(O)_2R^c]_2$, —$N(R^g)S(O)_2OR^c$, —$N(R^g)S(O)_2NR^cR^c$, —$N(R^g)[S(O)_2]_2R^c$, —$N(R^g)C(O)OR^c$, —$N(R^g)C(O)SR^c$, —$N(R^g)C(O)NR^cR^c$, —$N(R^g)C(O)NR^c$,—$NR^cR^c$, —$N(R^g)N(R^g)C(O)NR^cR^c$, —$N(R^g)C(S)NR^cR^c$, —$[N(R^g)C(O)]_2R^c$, —$N(R^g)[C(O)]_2R^c$, —$N\{[C(O)]_2R^c\}_2$, —$N(R^g)[C(O)]_2OR^c$, —$N(R^g)[C(O)]_2NR^cR^c$, —$N\{[C(O)]_2OR^c\}_2$, —$N\{[C(O)]_2NR^cR^c\}_2$, —$[N(R^g)C(O)]_2OR^c$, —$N(R^g)C(NR^g)OR^c$, —$N(R^g)C(NOH)R^c$, —$N(R^g)C(NR^g)SR^c$, —$N(R^g)C(NR^g)NR^cR^c$ and —N=$C(R^g)NR^cR^c$ and each $R^c$ independently of one another denotes hydrogen or a group optionally substituted by one or more identical or different $R^d$ and/or $R^e$, selected from among $C_{1-6}$alkyl, 2-6 membered heteroalkyl, $C_{1-6}$haloalkyl, $C_{3-10}$Cycloalkyl, $C_{4-16}$Cycloalkylalkyl, $C_{6-10}$-aryl, $C_{7-16}$arylalkyl, 5-12 membered hetero-aryl, 6-18 membered heteroarylalkyl, 3-14 membered heterocycloalkyl and 4-14 membered heterocycloalkylalkyl, and each $R^d$ denotes a suitable group and is selected independently of one another from among =O, —$OR^e$, $C_{1-3}$haloalkyloxy, —$OCF_3$, =S, —$SR^e$, =$NR^e$, =$NOR^e$, =$NNR^eR^e$, =$NN(R^g)C(O)NR^eR^e$, —$NR^eR^e$, —$ONR^e$ $R^e$, —$N(R^g)NR^eR^e$, halogen, —$CF_3$, —CN, —NC, —OCN, —SCN, —NO, —$NO_2$, =$N_2$, —$N_3$, —$S(O)$ $R^e$, —$S(O)OR^e$, —$S(O)_2R^e$, —$S(O)_2OR^e$, —$S(O)NR^e$ $R^e$, —$S(O)_2NR^eR^e$, —$OS(O)R^e$, —$OS(O)_2R^e$, —$OS(O)_2OR^e$, —$OS(O)NR^eR^e$, —$OS(O)_2NR^eR^e$, —$C(O)$ $R^e$, —$C(O)OR^e$, —$C(O)SR^e$, —$C(O)NR^eR^e$, —$C(O)N(R^g)NR^eR^e$, —$C(O)N(R^g)OR^e$, —$C(NR^g)NR^eR^e$, —$C(NOH)R^e$, —$C(NOH)NR^eR^e$, —$OC(O)R^e$, —$OC(O)OR^e$, —$OC(O)SR^e$, —$OC(O)NR^eR^e$, —$OC(NR^g)NR^eR^e$, —$SC(O)R^e$, —$SC(O)OR^e$, —$SC(O)NR^eR^e$, —$SC(NR^g)NR^eR^e$, —$N(R^g)C(O)R^e$, —$N[C(O)R^e]_2$, —$N(OR^g)C(O)R^e$, —$N(R^g)C(NR^g)R^e$, —$N(R^g)N(R^g)C(O)R^e$, —$N[C(O)R^e]NR^eR^e$, —$N(R^g)C(S)R^e$, —$N(R^g)S(O)R^e$, —$N(R^g)S(O)OR^e$—$N(R^g)S(O)_2R^e$, —$N[S(O)_2R^e]_2$, —$N(R^g)S(O)_2OR^e$, —$N(R^g)S(O)_2NR^e$ $R^e$, —$N(R^g)[S(O)_2]_2R^e$, —$N(R^g)C(O)OR^e$, —$N(R^g)C(O)SR^e$, —$N(R^g)C(O)NR^eR^e$, —$N(R^g)C(O)NR^gNR^e$ $R^e$, —$N(R^g)N(R^g)C(O)NR^eR^e$, —$N(R^g)C(S)NR^eR^e$, —$[N(R^g)C(O)]_2R^e$, —$N(R^g)[C(O)]_2R^e$, —$N\{[C(O)]_2R^e\}_2$, —$N(R^g)[C(O)]_2OR^e$, —$N(R^g)[C(O)]_2NR^eR^e$, —$N\{[C(O)]_2OR^e\}_2$, —$N\{[C(O)]_2NR^eR^e\}_2$, —$[N(R^g)C(O)]_2OR^e$, —$N(R^g)C(NR^g)OR^e$, —$N(R^g)C(NOH)R^e$, —$N(R^g)C(NR^g)SR^e$, —$N(R^g)C(NR^g)NR^eR^e$ and —N=$C(R^g)NR^eR^e$ each $R^e$ independently of one another denotes hydrogen or a group optionally substituted by one or more identical or different $R^f$ and/or $R^g$, selected from among $C_{1-6}$alkyl, 2-6 membered heteroalkyl, $C_{1-6}$haloalkyl, $C_{3-10}$cycloalkyl, $C_{4-16}$cycloalkylalkyl, $C_{6-10}$aryl, $C_{7-16}$arylalkyl, 5-12 membered hetero-aryl, 6-18 membered heteroarylalkyl, 3-14 membered heterocycloalkyl and 4-14 membered heterocycloalkylalkyl, and each $R^f$ denotes a suitable group and in each case is selected independently of one another from among =O, —$OR^g$, $C_{1-3}$haloalkyloxy, —$OCF_3$, =S, —$SR^g$, =$NR^g$, =$NOR^g$, =$NNR^gR^g$, =$NN(R^h)C(O)NR^gR^g$, —$NR^g$ $R^g$, —$ONR^gR^g$, —$N(R^h)NR^gR^g$, halogen, —$CF_3$, —CN, —NC, —OCN, —SCN, —NO, —$NO_2$, =$N_2$, —$N_3$, —$S(O)R^g$, —$S(O)OR^g$, —$S(O)_2R^g$, —$S(O)_2OR^g$, —$S(O)NR^gR^g$, —$S(O)_2NR^gR^g$, —$OS(O)R^g$, —$OS(O)_2R^g$, —$OS(O)_2OR^g$, —$OS(O)NR^gR^g$, —$OS(O)_2NR^gR^g$, —$C(O)R^g$, —$C(O)OR^g$, —$C(O)SR^g$, —$C(O)NR^gR^g$, —$C(O)N(R^h)NR^gR^g$, —$C(O)N(R^h)OR^g$, —$C(NR^h)NR^gR^g$, —$C(NOH)R^g$, —$C(NOH)NR^g$ $R^g$, —$OC(O)R^g$, —$OC(O)OR^g$, —$OC(O)SR^g$, —$OC(O)NR^gR^g$, —$OC(NR^h)NR^gR^g$, —$SC(O)R^g$, —$SC(O)OR^g$, —$SC(O)NR^gR^g$, —$SC(NR^h)NR^gR^g$, —$N(R^h)C(O)R^g$, —$N[C(O)R^g]_2$, —$N(OR^h)C(O)R^g$, —$N(R^h)C(NR^h)R^g$, —$N(R^h)N(R^h)C(O)R^g$, —$N[C(O)R^g]NR^gR^g$, —$N(R^h)C(S)R^g$, —$N(R^h)S(O)R^g$, —$N(R^h)S(O)OR^g$, —$N(R^h)S(O)_2R^g$, —$N[S(O)_2R^g]_2$, —$N(R^h)S(O)_2OR^g$, —$N(R^h)S(O)_2NR^gR^g$, —$N(R^h)[S(O)_2]_2R^g$, —$N(R^h)C(O)OR^g$, —$N(R^h)C(O)SR^g$, —$N(R^h)C(O)NR^gR^g$, —$N(R^h)C(O)NR^hNR^gR^g$, —$N(R^h)N(R^h)C(O)NR^gR^g$, —$N(R^h)C(S)NR^gR^g$, —$[N(R^h)C(O)]_2R^g$, —$N(R^h)[C(O)]_2R^g$, —$N\{[C(O)]_2R^g\}_2$, —$N(R^h)[C(O)]_2OR^g$, —$N(R^h)[C(O)]_2NR^gR^g$, —$N\{[C(O)]_2OR^9\}_2$, —$N\{[C(O)]_2NR^gR^g\}_2$, —$[N(R^h)C(O)]_2OR^g$, —$N(R^h)C(NR^h)OR^g$, —$N(R^h)C(NOH)R^g$, —$N(R^h)C(NR^h)SR^g$, —$N(R^h)C(NR^h)NR^gR^g$; and —N=$C(R^h)NR^hR^h$; and each $R^g$ independently of one another denotes hydrogen or a group optionally substituted by one or more identical or different $R^h$, selected from among $C_{1-6}$alkyl, 2-6 membered heteroalkyl, $C_{1-6}$haloalkyl, $C_{3-10}$cycloalkyl, $C_{4-16}$cycloalkylalkyl, $C_{6-10}$-aryl, $C_{7-16}$arylalkyl, 5-12 membered hetero-aryl, 6-18 membered heteroarylalkyl, 3-14 membered heterocycloalkyl and 4-14 membered heterocycloalkylalkyl; and each $R^h$ is selected independently of one another from among hydrogen, $C_{1-6}$alkyl, 2-6 membered heteroalkyl, $C_{1-6}$haloalkyl, $C_{3-10}$cycloalkyl, $C_{4-16}$cycloalkylalkyl, $C_{6-10}$-aryl, $C_{7-16}$arylalkyl, 5-12 membered heteroaryl, 6-18 membered heteroarylalkyl, 3-14 membered heterocycloalkyl and 4-14 membered heterocycloalkylalkyl, optionally in the form of the tautomers, the racemates, the enantiomers, the diastereomers, the prodrugs and the mixtures thereof, and optionally the pharmacologically acceptable salts thereof.

2. The compound according to claim 1, wherein X is selected from a group consisting of —$(CH_2)_2$— and —$(CH_2)_3$—, optionally substituted by $C_{1-6}$alkyl.

3. The compound according to claim 1, wherein $R^3$ is a radical selected from the group consisting of $C_{6-10}$aryl and 5-12 membered heteroaryl, optionally substituted by one or more $R^4$.

4. The compound according to claim 3, wherein $R^3$ is pyridyl, pyrimidyl or pyrazolyl.

5. The compound according to claim 1, wherein $R^3$ is substituted by a residue selected from the group consisting of halogen, —CN, —$OR^c$, —$NR^cR^c$ and $C_{1-6}$alkyl optionally substituted by $R^b$.

6. The compound according to claim 1, wherein $R^3$ is hydrogen.

7. The compound according to claim 1, wherein $R^1$ is selected from the group consisting of —NHC(O)$R^c$, —NHC(O)O$R^c$, —NHC(O)N$R^c R^c$ and —C(O)N$R^c R^c$.

8. The compound according to claim 7, wherein $R^1$ is —NHC(O)CH$_3$.

9. The compound according to claim 1, wherein $R^4$ is selected from the group consisting of $C_{1-6}$alkyl, $C_{3-10}$cycloalkyl, $C_{6-10}$aryl, 5-12 membered heteroaryl and 3-14 membered heterocycloalkyl.

* * * * *